United States Patent [19]
Iwata et al.

[11] Patent Number: 5,496,951
[45] Date of Patent: Mar. 5, 1996

[54] 4-OXOQUINOLINE-3-CARBOXYLIC ACID DERIVATIVES THEIR PREPARATION AND THEIR USE

[75] Inventors: Masayuki Iwata, Tokyo; Tomio Kimura, Ube; Teruhiko Inoue, Ube; Yoshimi Fujihara, Ube; Tetsushi Katsube, Ube, all of Japan

[73] Assignees: Sankyo Company, Limited, Tokyo; Ube Industries Limited, Ube, both of Japan

[21] Appl. No.: 379,975

[22] Filed: Jan. 27, 1995

Related U.S. Application Data

[62] Division of Ser. No. 227,678, Apr. 14, 1994, Pat. No. 5,436,367, which is a division of Ser. No. 594,283, Oct. 9, 1990, Pat. No. 5,348,961, which is a division of Ser. No. 381,025, Jul. 17, 1989, abandoned.

[30] Foreign Application Priority Data

Jul. 20, 1988 [JP] Japan .................................. 63-180557
Sep. 7, 1988 [JP] Japan .................................. 63-224220

[51] Int. Cl.⁶ ................................................ C07D 215/56
[52] U.S. Cl. .......................................... 546/13; 546/156
[58] Field of Search ........................................ 546/156, 13

[56] References Cited

FOREIGN PATENT DOCUMENTS 0230295 7/1987 European Pat. Off. .
0241206 10/1987 European Pat. Off. .
0265230 2/1988 European Pat. Off. .
0302525 1/1989 European Pat. Off. .

*Primary Examiner*—Bernard Dentz
*Attorney, Agent, or Firm*—Frishauf, Holtz, Goodman, Langer & Chick

[57] ABSTRACT

Compounds of formula (I):

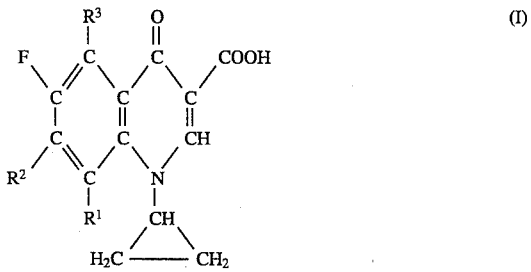

(in which: $R^1$ represents fluorinated methoxy: $R^2$ represents a nitrogen-containing heterocyclic group and $R^3$ represents hydrogen or amino) and pharmaceutically acceptable salts, esters and amides thereof are valuable antibacterial agents, which may be prepared by reacting a compound similar to that of formula (I) but in which $R^2$ is replaced by a halogen atom with a compound providing the required group $R^2$.

15 Claims, No Drawings

4-OXOQUINOLINE-3-CARBOXYLIC ACID DERIVATIVES THEIR PREPARATION AND THEIR USE

This is a division of application Ser. No. 08/227,678 filed Apr. 14, 1994, now U.S. Pat. No. 5,436,367, which is a division of Ser. No. 07/594,283 filed Oct. 9, 1990, now U.S. Pat. No. 5,348,961, which is a division of application Ser. No. 07/381,025 filed Jul. 17, 1989, now abandoned.

BACKGROUND OF THE INVENTION

The present invention relates to a series of novel 8-(fluorinated methoxy)-4-oxoquinoline-carboxylic acid derivatives which have been found to have valuable and powerful antibacterial activity. The invention also provides compositions containing these compounds, methods of using them and processes for preparing them.

The compounds of the present invention are 1-cyclopropyl-4-oxo-6-fluoro-7-(optionally substituted heterocyclic)-8-(fluorinated methoxy)-quinoline-3-carboxylic acid derivatives and 1-cyclopropyl-4-oxo-5-amino- 6-fluoro-7-(optionally substituted heterocyclic)-8-(fluorinated methoxy)-quinoline- 3-carboxylic acid derivatives.

It is an unfortunate fact of modern medicine that many infectious bacteria are gradually developing resistance to the antibiotics commonly used to treat infection caused by them, with the result that known antibacterial agents are increasingly becoming of limited effectiveness. There is, therefore, a continuing need to develop new antibacterial agents, which may, even if only for a restricted period, be effective against infectious bacteria. Most of the common antibacterial agents in present day use were originally developed from fermentation products, although some are of wholly synthetic origin.

There have been proposals to use certain 4-oxoquinoline-3-carboxylic acid derivatives as antibacterial agents. For example, European Patent Publication No. 78 362 discloses a limited class of 1-cyclopropyl-6-fluoro-1,4-dihydro-4-oxo- 7-(1-piperazinyl)quinoline-3-carboxylic acid derivatives, in which the piperazinyl group is unsubstituted or has a methyl, ethyl or β-hydroxyethyl substituent at the 4-position. These compounds resemble certain of those of the present invention, except that they lack the 8-fluorinated methoxy group which has been found to be critical to the achievement of the excellent activity of the compounds of the present invention.

European Patent Publications No. 106 489, No. 153 163. No. 230 295, No. 235 762 and No. 241 206 disclose classes of quinoline derivatives, including amongst many others, some 1-substituted-4-oxo-1,4-dihydro- 6-halo-7-(optionally substituted heterocyclic)-8-substituted-quinoline-3-carboxylic acid derivatives, of which in some the 8-substituent is an alkoxy group, but do not disclose any compounds in which the 8-substituent is a fluorinated methoxy group. Of the compounds disclosed in European Patent Publication No. 78 362, one, namely Norfloxacin, whose systematic name is 1-ethyl-6-fluoro-1,4-dihydro-4-oxo-7-(1-piperazinyl)-quinoline-3-carboxylic acid, is disclosed in The Merck Index Tenth Edition, published in 1983, monograph number 6541. In common with the other compounds of European Patent Publication No 78 362, this lacks the critical 8-fluorinated methoxy substituent of the present invention.

We have surprisingly found that the combination of a limited class of 8-fluorinated methoxy substituents with certain limited and highly specific classes of heterocyclic substituent at the 7-position and optionally an amino group at the 5-position leads to the production of compounds which have unexpectedly good antibacterial activities against Gram positive and Gram negative bacteria, in many cases far surpassing those of the prior art compounds. In particular, the compounds of the present invention have surprisingly good activity against several Gram positive bacteria against which the known compounds are ineffective or are effective only at high concentrations, for example *Staphylococcus aureus* and *Enterococcus faecalis*.

It is believed that the closest prior art is the aforementioned European Patent Publications No. 78 362, No. 230 295 and No. 241 206. We have surprisingly found that the compounds of the present invention show an exceptional antibacterial activity against penicillin- and cephalosporin-resistant Gram positive bacteria and *Pseudomonas aeruginosa*, which can be controlled only with difficulty with β-lactam antibiotics, and which are, therefore, a major problem in medicine.

BRIEF SUMMARY OF INVENTION

It is, therefore, an object of the present invention to provide a series of 1,4-dihydro-4-oxoquinoline-3-carboxylic acid derivatives which have exceptional antibacterial activity.

It is a further object of the invention to provide pharmaceutical compositions containing such a quinoline derivative as an antibacterial agent.

It is a still further object of the present invention to provide methods for the treatment or prophylaxis of bacterial infections in animals (including human beings) by the administration thereto of such a quinoline derivative.

The compounds of the present invention are those compounds of formula (I):

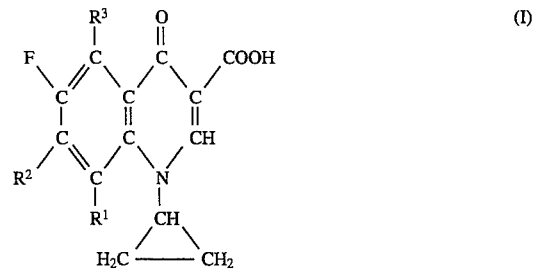

in which $R^1$ represents a methoxy group having at least one fluorine substituent:

$R^2$ represents a group selected from the group consisting of:

(i) groups of formula (II)

in which:

$R^4$ represents a hydrogen atom; a hydroxy group; an amino group; a $C_1$–$C_6$ alkyl group; a substituted $C_1$–$C_6$ alkyl group having at least one substituent selected from the group consisting of substituents (a), defined below; an aralkyl group; a $C_1$–$C_6$ aliphatic acyl group; or a substituted $C_2$–$C_6$ aliphatic acyl group having at least one substituent selected from the group consisting of substituents (a), defined below;

$R^5$ represents a hydrogen atom, a $C_1$–$C_6$ alkyl group or a substituted $C_1$–$C_6$ alkyl group having at least one substituent selected from the group consisting of substituents (b), defined below;

A represents an ethylene group, a trimethylene group, or a group of formula —$COCH_2$—, and m represents 1 or 2;

(ii) groups of formula (III):

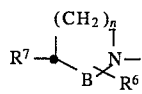 (III)

in which:

$R^6$ represents a hydrogen atom; a $C_1$–$C_6$ alkyl group; a substituted $C_1$–$C_6$ alkyl group having at least one substituent selected from the group consisting of substituents (b), defined below; a hydroxy group; a $C_1$–$C_6$ alkoxy group; or a $C_1$–$C_6$ alkoxy group having at least one fluorine substituent;

$R^7$ represents a group of formula $R^8R^9N$—$(CH_2)_q$—, in which $R^8$ and $R^9$ are independently selected from the group consisting of hydrogen atoms. $C_1$–$C_6$ alkyl groups and aralkyl groups, and q represents 0 or 1; a hydroxy group; or a $C_1$–$C_6$ alkoxy group;

B represents a methylene group, an ethylene group, a trimethylene group, or a tetramethylene group; and n represents 1 or 2;

(iii) groups of formula (IV):

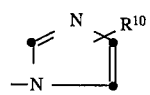 (IV)

in which:

$R^{10}$ represents a hydrogen atom or a $C_1$–$C_6$ alkyl group; and (iv) groups of formula (V):

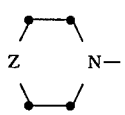 (V)

in which:

Z represents a oxygen atom or a sulfur atom;

$R^3$ represents a hydrogen atom or an amino group;

substituents (a):

hydroxy groups, $C_1$–$C_6$ alkoxy groups, $C_2$–$C_6$ aliphatic acyloxy groups, $C_1$–$C_6$ aliphatic acyl groups, carboxy groups, $C_2$–$C_6$ alkoxycarbonyl groups, sulfo groups, amino groups, $C_2$–$C_6$ aliphatic acylamino groups, and mono- and di-($C_1$–$C_6$ alkyl) substituted amino groups;

substituents (b):

hydroxy groups, $C_1$–$C_6$ alkoxy groups, and halogen atoms; and said aralkyl groups have from 1 to 4 carbon atoms in the alkyl part and have an aryl part which has from 6 to 10 carbon atoms and which is unsubstituted or has at least one substituent selected from the group consisting of substituents (c), defined below;

substituents (c):

hydroxy groups, $C_1$–$C_6$ alkyl groups, $C_1$–$C_6$ alkoxy groups, $C_2$–$C_6$ aliphatic acyloxy groups, $C_1$–$C_6$ aliphatic acyl groups, carboxy groups, $C_2$–$C_6$ alkoxycarbonyl groups, sulfo groups, nitro groups, cyano groups, amino groups, $C_2$–$C_6$ aliphatic acylamino groups, and mono- and di-($C_1$–$C_6$ alkyl) substituted amino groups;

and pharmaceutically acceptable salts, esters and amides thereof.

The invention also provides a pharmaceutical composition for the treatment of bacterial infections, comprising an effective amount of an antibacterial agent in combination with a pharmaceutically acceptable carrier or diluent, wherein the antibacterial agent is selected from the group consisting of compounds of formula (I) and pharmaceutically acceptable salts, esters and amides thereof.

The invention still further provides a method for the treatment or prophylaxis of bacterial infection comprising administering an amount of an antibacterial agent to an animal (which may be a mammal, e.g. human) sufficient to exert an antibacterial effect, wherein said antibacterial agent is selected from the group consisting of compounds of formula (I) and pharmaceutically acceptable salts, esters and amides thereof.

The invention also provides methods of preparing the compounds of the invention, which are described in more detail hereafter.

DETAILED DESCRIPTION OF INVENTION

In the compounds of the present invention, $R^1$ represents a methoxy group having at least one fluorine substituent, which may be a monofluoromethoxy group, a difluoromethoxy group or a trifluoromethoxy group of which the difluoromethoxy and trifluoromethoxy groups are preferred.

Where $R^2$ represents a group of formula (II) and $R^4$ represents an alkyl group, this may be a straight or branched chain alkyl group containing from 1 to 6, preferably from 1 to 4, carbon atoms, and examples of such groups include the methyl, ethyl, propyl, isopropyl, butyl, isobutyl, pentyl, isopentyl, t-pentyl, hexyl and 1,3-dimethylbutyl groups. Of these, the methyl, ethyl, propyl, isopropyl, butyl and isobutyl groups are preferred. Such alkyl groups may be unsubstituted or may have at least one substituent selected from the group consisting of substituents (a), defined above, that is:

hydroxy groups;

straight and branched chain alkoxy groups containing from 1 to 6, preferably from 1 to 3, carbon atoms such as the methoxy, ethoxy, propoxy, isopropoxy, butoxy, isobutoxy, pentyloxy, isopentyloxy, t-pentyloxy and hexyloxy groups. Of these, the methoxy, ethoxy, propoxy and isopropoxy groups are preferred;

aliphatic acyloxy groups containing from 2 to 6, preferably from 2 to 4, carbon atoms such as the acetoxy, propionyloxy, butyryloxy, isobutyryloxy, valeryloxy, isovaleryloxy, pivaloyloxy and hexanoyloxy groups, of which the acetoxy, propionyloxy, butyryloxy and isobutyryloxy groups are preferred;

aliphatic acyl groups containing from 1 to 6, preferably from 1 to 4, carbon atoms such as the formyl, acetyl, propionyl, butyryl, isobutyryl, valeryl, isovaleryl, pivaloyl and hexanoyl groups, of which the formyl, acetyl, propionyl, butyryl and isobutyryl groups are preferred;

carboxy groups;

alkoxycarbonyl groups containing a total of from 2 to 6, preferably from 2 to 4, carbon atoms (i.e. the alkoxy part has from 1 to 5, preferably from 1 to 3, carbon atoms), such as the methoxycarbonyl, ethoxycarbonyl, propoxycarbonyl, isopropoxycarbonyl, butoxycarbonyl, isobutoxycarbonyl, t-butoxycarbonyl and pentyloxycarbonyl groups, of which the methoxycarbonyl, ethoxycarbonyl, propoxycarbonyl and isopropoxycarbonyl groups are preferred;

sulfo groups;

amino groups;

aliphatic acylamino groups containing from 2 to 6, preferably from 2 to 4, carbon atoms such as acetoamido, propionamido, butyramido, isobutyramido, valeramido, isovaleramido and pivaloylamino groups, of which the acetoamido, propionamido, butyramido and isobutyramido groups are preferred; and mono- and di-alkyl-substituted amino groups in which the or each alkyl group contains from 1 to 6, preferably from 1 to 4, carbon atoms such as the methylamino, ethylamino, propylamino, isopropylamino, butylamino, isobutylamino, dimethylamino, diethylamino, dipropylamino, diisopropylamino, pentylamino and hexylamino groups, of which the methylamino, dimethylamino, ethylamino, propylamino, isopropylamino, butylamino and isobutylamino groups are preferred.

Where $R^4$ represents an aralkyl group, this has from 1 to 4 alkyl groups in the alkyl part and from 6 to 10 carbon atoms in the aryl part. Examples of such groups include the benzyl, phenethyl, 1-phenylethyl, 1-phenylpropyl, 2-phenylpropyl, 3-phenylpropyl, 4-phenylbutyl, 1-naphthylmethyl and 2-naphthylmethyl groups. These groups may be unsubstituted or may have at least one substituent on the aryl part selected from the group consisting of substituents (c), defined above. Examples of the groups which may be included in substituents (c) are as exemplified in relation to the same groups included in substituents (a), as well as $C_1$–$C_6$ alkyl groups, such as those exemplified in relation to the alkyl groups which may be represented by $R^4$nitro groups and cyano groups especially alkoxy groups, amino groups and mono- and di- alkylamino groups. Examples of such groups include the benzyl, p-methoxybenzyl, p-aminobenzyl, p-methylaminobenzyl and p-dimethylaminobenzyl groups.

Where $R^4$ represents an aliphatic acyl group, this may contain from 1 to 6, preferably from 1 to 4, carbon atoms, and examples include the formyl, acetyl, propionyl, butyryl, isobutyryl, valeryl, isovaleryl, pivaloyl and hexanoyl groups, of which the formyl, acetyl, propionyl, butyryl and isobutyryl groups are preferred. These groups may be unsubstituted or may have at least one substituent selected from the group consisting of substituents (a), defined and exemplified above.

Where $R^2$ represents said group of formula (II) or said group of formula (IV), $R^5$ and $R^{10}$, respectively, may each represent a hydrogen atom or an alkyl group containing from 1 to 6, preferably from 1 to 3, carbon atoms. Examples of such groups include the methyl, ethyl, propyl, isopropyl, butyl, isobutyl, pentyl, isopentyl, t-pentyl, hexyl and 1,3-dimethylbutyl groups. Of these, the methyl, ethyl, propyl and isopropyl groups are preferred. $R^5$ may also represent such an alkyl group having at least one substituent selected from the group consisting of substituents (b), defined above, i.e.:

hydroxy groups;

straight and branched chain alkoxy groups containing from 1 to 6, preferably from 1 to 3, carbon atoms such as the methoxy, ethoxy, propoxy, isopropoxy, butoxy, isobutoxy, pentyloxy, isopentyloxy, t-pentyloxy and hexyloxy groups. Of these, the methoxy, ethoxy, propoxy and isopropoxy groups are preferred; and halogen atoms, such as the fluorine, chlorine, bromine and iodine atoms, of which the fluorine and chlorine atoms are preferred.

Where $R^2$ represents said group of formula (III), $R^6$ may represent: a hydrogen atom; an alkyl group containing from 1 to 6, preferably from 1 to 3, carbon atoms, such as the methyl, ethyl, propyl, isopropyl, butyl, isobutyl, pentyl, isopentyl, t-pentyl, hexyl and 1,3-dimethylbutyl groups, of which the methyl, ethyl, propyl and isopropyl groups are preferred; a substituted alkyl group having from 1 to 6 carbon atoms, which may be any of the unsubstituted groups exemplified above and in which the substituent is selected from the group consisting of substituents (b), defined and exemplified above; a hydroxy group; an alkoxy group containing from 1 to 6, preferably from 1 to 3, carbon atoms, such as the methoxy, ethoxy, propoxy, isopropoxy, butoxy, isobutoxy, pentyloxy, isopentyloxy, t-pentyloxy and hexyloxy groups, of which the methoxy, ethoxy, propoxy and isopropoxy groups are preferred; or an alkoxy group containing from 1 to 6, preferably from 1 to 3, carbon atoms and having at least one fluorine substituent, such as the fluoromethoxy, difluoromethoxy, trifluoromethoxy, 1-fluoroethoxy, 2-fluoroethoxy, 2,2-difluoroethoxy, 2,2,2-trifluoroethoxy, 3-fluoropropoxy, 4-fluorobutoxy, 5-fluoropentyloxy, 6-fluorohexyloxy, 3,3-difluoropropoxy, 3,3,3-trifluoropropoxy, 4,4-difluorobutoxy and 4,4,4-trifluorobutoxy groups, of which the fluoromethoxy, difluoromethoxy, trifluoromethoxy, 1-fluoroethoxy, 2-fluoroethoxy, 2,2-difluoroethoxy and 2,2,2-trifluoroethoxy groups are preferred.

Where $R^2$ represents said group of formula (III) and $R^7$ represents said group of formula $R^8R^9N$—$(CH_2)_q$—, $R^8$ and $R^9$ may be the same or different and each represents; a hydrogen atom: an alkyl group containing from 1 to 6, preferably from 1 to 3, carbon atoms, such as the methyl, ethyl, propyl, isopropyl, butyl, isobutyl, pentyl, isopentyl, t-pentyl, hexyl and 1,3-dimethylbutyl groups, of which the methyl, ethyl, propyl and isopropyl groups are preferred; or an aralkyl group, which may be as defined and exemplified above in relation to the aralkyl groups which may be represented by $R^4$, and may optionally be substituted by at least one substituent selected from the group consisting of substituents (c), defined and exemplified above, and preferably with a $C_1$–$C_6$ alkoxy group, an amino group, or a mono- or di-($C_1$–$C_6$) alkylamino group such as the benzyl, p-methoxybenzyl, p-aminobenzyl, p-methylaminobenzyl and p-dimethylaminobenzyl groups.

Alternatively, $R^7$ may represent: a hydroxy group; or an alkoxy group containing from 1 to 6, preferably from 1 to 3, carbon atoms such as the methoxy, ethoxy, propoxy, isopropoxy, butoxy, isobutoxy, pentyloxy, isopentyloxy, t-pentyloxy and hexyloxy groups, of which the methoxy, ethoxy, propoxy and isopropoxy groups are preferred.

In the group of formula (V), Z may be an oxygen atom or a sulfur atom; where it is an oxygen atom, the group is the morpholino group; where it is a sulfur atom, the group is a thiomorpholino (i.e. perhydro-1,4-thiazin-4-yl) group.

Of the compounds of formula (I), the preferred compounds are those in which $R^2$ represents:

a group of formula (II):

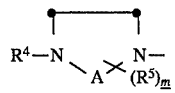

(II)

(in which $R^4$, $R^5$, A and m are as defined above);

a group of formula (IIIa):

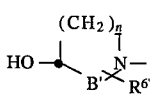

(in which: $R^{6'}$ represents a hydrogen atom or an alkyl group having from 1 to 3 carbon atoms; B' represents a methylene group or an ethylene group; and n is as defined above);

a group of formula (IIIb):

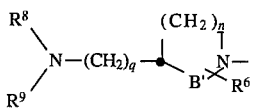

(in which $R^6$, $R^8$, $R^9$, B', n and q are as defined above);

a group of formula (IIIc):

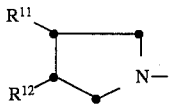

(in which: $R^{11}$ and $R^{12}$ are independently selected from the group consisting of hydroxy groups and alkoxy groups having from 1 to 3 carbon atoms);

a group of formula (IVa):

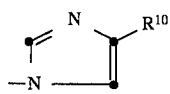

(in which $R^{10}$ is as defined above); or a group of formula (V):

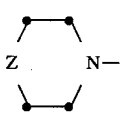

(in which Z is as defined above).

We also prefer those compounds of formula (I) in which $R^1$ represents a difluoromethoxy group or a trifluoromethoxy group, and especially those in which $R^1$ represents a difluoromethoxy group or a trifluoromethoxy group and $R^2$ represents a group of formula (II), (IIIa), (IIIb), (IIIc), (IVa) or (V), as defined above, both where $R^3$ represents a hydrogen atom and where it represents an amino group.

The compounds of the invention contain one carboxy group at the 3-position of the quinoline ring. This carboxy group may form esters, amides and salts.

Where the carboxy group is esterified, the nature of the resulting ester is not critical to the present invention. In principle, the compounds of the invention, being carboxylic acids, will form esters with any ester-forming alcohol and all such esters form part of the present invention. However, where the esters are to be employed for therapeutic purposes, it is, of course, necessary that the resulting esters should be pharmaceutically acceptable, which, as is well understood in the art, means that the esters should not have reduced activity (or unacceptably reduced activity) and should not have increased toxicity (or unacceptably increased toxicity) as compared with the free acid. However, where the ester is to be employed for other purposes, for example as an intermediate in the preparation of other compounds, even this criterion does not apply.

Examples of such esters include: $C_1$–$C_6$, more preferably $C_1$–$C_4$, alkyl esters, for example the methyl, ethyl, propyl, isopropyl, butyl, isobutyl, sec-butyl, t-butyl, pentyl and hexyl esters; aralkyl (including diarylalkyl) esters, such as the benzyl, p-nitrobenzyl and benzhydryl esters; lower aliphatic acyloxyalkyl groups, such as the acetoxymethyl or pivaloyloxymethyl groups; alkoxycarbonylalkyl esters, in which the alkoxy and alkyl parts are both $C_1$–$C_4$, especially alkoxycarbonylmethyl and 1-(alkoxycarbonyl)ethyl esters, such as the ethoxycarbonylmethyl and t-butoxycarbonylmethyl esters; alkoxycarbonyloxyalkyl esters in which the alkoxy and alkyl parts are both $C_1$–$C_4$, especially the 1- and 2-(alkoxycarbonyloxy)ethyl esters, such as the 1-(ethoxycarbonyloxy)ethyl, 1-(isopropoxycarbonyloxy)ethyl, 2-methoxycarbonyloxyethyl, 2-ethoxycarbonyloxyethyl and 2-t-butoxycarbonyloxyethyl esters; N,N-di-substituted aminocarbonylalkyl esters, in which the alkyl group is $C_1$–$C_6$, preferably $C_1$–$C_4$, and the substituents on the amino group are preferably $C_1$–$C_4$ alkyl groups such as the N,N-dimethylaminocarbonylmethyl esters; and other specific esters, such as the phthalidyl, substituted phthalidyl, phenacyl, substituted phenacyl (e.g. p-nitrophenacyl), (5-phenyl-2-oxo-1,3-dioxolen-4-yl)methyl and (5-methyl-2-oxo-1,3-dioxolen-4-yl)methyl esters.

Likewise, where the carboxy group has formed an amide, the precise nature of the amide is not critical, provided that, where the amide is to be used for therapeutic purposes, the resulting amide is pharmaceutically acceptable. Accordingly, the carboxy group can be replaced by a carbamoyl group or a substituted carbamoyl group, preferably an alkylcarbamoyl or dialkylcarbamoyl group in which the or each alkyl group is a $C_1$–$C_3$ alkyl group (e.g. as defined above in relation to $R^4$), for example a methylcarbamoyl, ethylcarbamoyl, dimethylcarbamoyl or diethylcarbamoyl group.

The carboxy group may also form salts with appropriate bases. The nature of such salts is likewise not critical, provided that, where they are to be used for therapeutic purposes, the salts are pharmaceutically acceptable. Examples of salts with bases include: salts with metals, especially alkali metals and alkaline earth metals, such as lithium, sodium, potassium, calcium and magnesium, and other metals, such as manganese, iron and aluminum; the ammonium salt; salts with organic amines, such as cyclohexylamine, diisopropylamine or triethylamine; and salts with basic amino acids, such as lysine or arginine.

The compounds of the invention contain a basic nitrogen atom and hence can also form acid addition salts. The nature of such salts is likewise not critical to the present invention, except that, where the salts are to be used for therapeutic purposes, they must be pharmaceutically acceptable. A wide variety of acids may be employed to form such salts and representative examples of such acids include: mineral acids, such as hydrochloric acid, hydrobromic acid, hydroiodic acid, phosphoric acid, metaphosphoric acid, nitric acid or sulfuric acid; organic carboxylic acids, such as acetic acid, oxalic acid, tartaric acid, citric acid, benzoic acid, glycolic acid, gluconic acid, glucuronic acid, succinic acid, maleic acid or fumaric acid; and organic sulfonic acids, such as methanesulfonic acid, ethanesulfonic acid, benzenesulfonic acid or p-toluenesulfonic acid. Such acid addition salts may be prepared by conventional methods.

The compounds of the invention may also exist in the form of hydrates and these likewise form part of the present invention.

Specific examples of compounds of the invention are given by the foregoing formula (I), in which the substituents are as defined in the following Table 1. In the Table, the following abbreviations are used:

TABLE 1

| Cpd No. | R¹ | R³ | R² |
|---|---|---|---|
| 1 | OCHF₂ | H | 1-Piz |
| 2 | OCHF₂ | H | 3-Me-1-Piz |
| 3 | OCHF₂ | H | 3,5-diMe-1-Piz |
| 4 | OCHF₂ | H | 2,5-diMe-1-Piz |
| 5 | OCHF₂ | H | 4-Me-1-Piz |
| 6 | OCHF₂ | H | 3,4-diMe-1-Piz |
| 7 | OCHF₂ | H | 3,4,5-triMe-1-Piz |
| 8 | OCHF₂ | H | 4-Et-1-Piz |
| 9 | OCHF₂ | H | 4-(2-HOEt)-1-Piz |
| 10 | OCHF₂ | H | 4-(2-MeOEt)-1-Piz |
| 11 | OCHF₂ | H | 4-(2-AcOEt)-1-Piz |
| 12 | OCHF₂ | H | 4-(2-NH₂Et)-1-Piz |
| 13 | OCHF₂ | H | 4-(2-NMe₂Et)-1-Piz |
| 14 | OCHF₂ | H | 4-(4-NH₂Bz)-1-Piz |
| 15 | OCHF₂ | H | 4-HCO-1-Piz |
| 16 | OCHF₂ | H | 4-Ac-1-Piz |
| 17 | OCHF₂ | H | 4-(AcMe)-1-Piz |
| 18 | OCHF₂ | H | 4-(EtcMe)-1-Piz |
| 19 | OCHF₂ | H | 4-(SfoMe)-1-Piz |
| 20 | OCHF₂ | H | 1-Diz |
| 21 | OCHF₂ | H | 4-Me-1-Diz |
| 22 | OCHF₂ | H | 3-oxo-1-Piz |
| 23 | OCHF₂ | H | 4-Me-3-oxo-1-Piz |
| 24 | OCHF₂ | H | 3-HO-1-Pyrd |
| 25 | OCHF₂ | H | 4-HO-1-Pip |
| 26 | OCHF₂ | H | 3,4-diHO-1-Pyrd |
| 27 | OCHF₂ | H | 3-HO-4-MeO-1-Pyrd |
| 28 | OCHF₂ | H | 3-NH₂-1-Azt |
| 29 | OCHF₂ | H | 3-NHMe-1-Azt |
| 30 | OCHF₂ | H | 3-NMe₂-1-Azt |
| 31 | OCHF₂ | H | 3-(NH₂Me)-1-Azt |
| 32 | OCHF₂ | H | 3-[(NHEt)Me]-1-Azt |
| 33 | OCHF₂ | H | 3-[(NMe₂)Me]-1-Azt |
| 34 | OCHF₂ | H | 3-NH₂-1-Pyrd |
| 35 | OCHF₂ | H | 3-NHEt-1-Pyrd |
| 36 | OCHF₂ | H | 3-NMe₂-1-Pyrd |
| 37 | OCHF₂ | H | 3-(NH₂Me)-1-Pyrd |
| 38 | OCHF₂ | H | 3-[(NHMe)Me]-1-Pyrd |
| 39 | OCHF₂ | H | 3-[(NHEt)Me]-1-Pyrd |
| 40 | OCHF₂ | H | 3-[(NMe₂)Me]-1-Pyrd |
| 41 | OCHF₂ | H | 3-NH₂-4-Me-1-Pyrd |
| 42 | OCHF₂ | H | 3-NH₂-4-HO-1-Pyrd |
| 43 | OCHF₂ | H | 3-NH₂-4-MeO-1-Pyrd |
| 44 | OCHF₂ | H | 3-NH₂-4-EtO-1-Pyrd |
| 45 | OCHF₂ | H | 4-NH₂-1-Pip |
| 46 | OCHF₂ | H | 4-NHMe-1-Pip |
| 47 | OCHF₂ | H | 4-NMe₂-1-Pip |
| 48 | OCHF₂ | H | 3-NH₂-1-Pip |
| 49 | OCHF₂ | H | 3-NHMe-1-Pip |
| 50 | OCHF₂ | H | 3-NH₂-1-Azp |
| 51 | OCHF₂ | H | 3-NH₂-3-Me-1-Pyrd |
| 52 | OCHF₂ | H | 1-Imid |
| 53 | OCHF₂ | H | 4-Me-1-Imid |
| 54 | OCHF₂ | H | Mor |
| 55 | OCHF₂ | H | Thz |
| 56 | OCHF₂ | H | 3-Et-1-Piz |
| 57 | OCHF₂ | H | 3,3-diMe-1-Piz |
| 58 | OCHF₂ | H | 3-iPr-1-Piz |
| 59 | OCHF₂ | H | 3-(MeOMe)-1-Piz |
| 60 | OCHF₂ | H | 4-(HCOMe)-3-Me-1-Piz |
| 61 | OCHF₂ | H | 3,5-di(CH₂F)-1-Piz |
| 62 | OCHF₂ | H | 4-NH₂-1-Piz |
| 63 | OCHF₂ | H | 4-HO-1-Piz |
| 64 | OCHF₂ | H | 4-(2-HOEt)-3-Me-1-Piz |
| 65 | OCHF₂ | H | 4-(2-MeOEt)-3-Me-1-Piz |
| 66 | OCHF₂ | H | 3-CH₂F-1-Piz |
| 67 | OCHF₂ | H | 4-NH₂-3-Me-1-Piz |
| 68 | OCHF₂ | H | 4-(HCOMe)-1-Piz |
| 69 | OCHF₂ | H | 4-HO-3-Me-1-Piz |
| 70 | OCHF₂ | H | 4-(AcMe)-3-Me-1-Piz |
| 71 | OCHF₂ | H | 3-Me-1-Diz |
| 72 | OCHF₂ | H | 3-NH₂-4-(MeOMe)-1-Pyrd |
| 73 | OCHF₂ | H | 3-NH₂-4-(CF₃CH₂O)-1-Pyrd |
| 74 | OCHF₂ | NH₂ | 1-Piz |
| 75 | OCHF₂ | NH₂ | 3-Me-1-Piz |
| 76 | OCHF₂ | NH₂ | 3,5-diMe-1-Piz |
| 77 | OCHF₂ | NH₂ | 2,5-diMe-1-Piz |
| 78 | OCHF₂ | NH₂ | 4-Me-1-Piz |
| 79 | OCHF₂ | NH₂ | 3,4-diMe-1-Piz |
| 80 | OCHF₂ | NH₂ | 3,4,5-triMe-1-Piz |
| 81 | OCHF₂ | NH₂ | 4-Et-1-Piz |
| 82 | OCHF₂ | NH₂ | 4-(2-HOEt)-1-Piz |
| 83 | OCHF₂ | NH₂ | 4-(2-MeOEt)-1-Piz |
| 84 | OCHF₂ | NH₂ | 4-(2-AcOEt)-1-Piz |
| 85 | OCHF₂ | NH₂ | 4-(2-NH₂Et)-1-Piz |
| 86 | OCHF₂ | NH₂ | 4-(2-NMe₂Et)-1-Piz |
| 87 | OCHF₂ | NH₂ | 4-(4-NH₂Bz)-1-Piz |
| 88 | OCHF₂ | NH₂ | 4-HCO-1-Piz |
| 89 | OCHF₂ | NH₂ | 4-Ac-1-Piz |
| 90 | OCHF₂ | NH₂ | 4-(AcMe)-1-Piz |
| 91 | OCHF₂ | NH₂ | 4-(EtcMe)-1-Piz |
| 92 | OCHF₂ | NH₂ | 4-(SfoMe)-1-Piz |
| 93 | OCHF₂ | NH₂ | 1-Diz |
| 94 | OCHF₂ | NH₂ | 4-Me-1-Diz |
| 95 | OCHF₂ | NH₂ | 3-oxo-1-Piz |
| 96 | OCHF₂ | NH₂ | 4-Me-3-oxo-1-Piz |
| 97 | OCHF₂ | NH₂ | 3-HO-1-Pyrd |
| 98 | OCHF₂ | NH₂ | 4-HO-1-Pip |
| 99 | OCHF₂ | NH₂ | 3,4-diHO-1-Pyrd |
| 100 | OCHF₂ | NH₂ | 3-HO-4-MeO-1-Pyrd |
| 101 | OCHF₂ | NH₂ | 3-NH₂-1-Azt |
| 102 | OCHF₂ | NH₂ | 3-NHMe-1-Azt |
| 103 | OCHF₂ | NH₂ | 3-NMe₂-1-Azt |
| 104 | OCHF₂ | NH₂ | 3-(NH₂Me)-1-Azt |
| 105 | OCHF₂ | NH₂ | 3-[(NHEt)Me]-1-Azt |
| 106 | OCHF₂ | NH₂ | 3-[(NMe₂)Me]-1-Azt |
| 107 | OCHF₂ | NH₂ | 3-NH₂-1-Pyrd |
| 108 | OCHF₂ | NH₂ | 3-NHEt-1-Pyrd |
| 109 | OCHF₂ | NH₂ | 3-NMe₂-1-Pyrd |
| 110 | OCHF₂ | NH₂ | 3-(NH₂Me)-1-Pyrd |
| 111 | OCHF₂ | NH₂ | 3-[(NHMe)Me]-1-Pyrd |
| 112 | OCHF₂ | NH₂ | 3-[(NHEt)Me]-1-Pyrd |
| 113 | OCHF₂ | NH₂ | 3-[(NMe₂)Me]-1-Pyrd |
| 114 | OCHF₂ | NH₂ | 3-NH₂-4-Me-1-Pyrd |
| 115 | OCHF₂ | NH₂ | 3-NH₂-4-HO-1-Pyrd |
| 116 | OCHF₂ | NH₂ | 3-NH₂-4-MeO-1-Pyrd |
| 117 | OCHF₂ | NH₂ | 3-NH₂-4-EtO-1-Pyrd |
| 118 | OCHF₂ | NH₂ | 4-NH₂-1-Pip |
| 119 | OCHF₂ | NH₂ | 4-NHMe-1-Pip |
| 120 | OCHF₂ | NH₂ | 4-NMe₂-1-Pip |
| 121 | OCHF₂ | NH₂ | 3-NH₂-1-Pip |
| 122 | OCHF₂ | NH₂ | 3-NHMe-1-Pip |
| 123 | OCHF₂ | NH₂ | 3-NH₂-1-Azp |
| 124 | OCHF₂ | NH₂ | 3-NH₂-3-Me-1-Pyrd |
| 125 | OCHF₂ | NH₂ | 1-Imid |
| 126 | OCHF₂ | NH₂ | 4-Me-1-Imid |
| 127 | OCHF₂ | NH₂ | Mor |
| 128 | OCHF₂ | NH₂ | Thz |
| 129 | OCHF₂ | NH₂ | 3-Et-1-Piz |
| 130 | OCHF₂ | NH₂ | 3,3-diMe-1-Piz |
| 131 | OCHF₂ | NH₂ | 3-iPr-1-Piz |
| 132 | OCHF₂ | NH₂ | 3-(MeOMe)-1-Piz |
| 133 | OCHF₂ | NH₂ | 4-(HCOMe)-3-Me-1-Piz |
| 134 | OCHF₂ | NH₂ | 3,5-di(CH₂F)-1-Piz |
| 135 | OCHF₂ | NH₂ | 4-NH₂-1-Piz |
| 136 | OCHF₂ | NH₂ | 4-HO-1-Piz |
| 137 | OCHF₂ | NH₂ | 4-(2-HOEt)-3-Me-1-Piz |
| 138 | OCHF₂ | NH₂ | 4-(2-MeOEt)-3-Me-1-Piz |
| 139 | OCHF₂ | NH₂ | 3-CH₂F-1-Piz |
| 140 | OCHF₂ | NH₂ | 4-NH₂-3-Me-1-Piz |
| 141 | OCHF₂ | NH₂ | 4-(HCOMe)-1-Piz |
| 142 | OCHF₂ | NH₂ | 4-HO-3-Me-1-Piz |
| 143 | OCHF₂ | NH₂ | 4-(AcMe)-3-Me-1-Piz |
| 144 | OCHF₂ | NH₂ | 3-Me-1-Diz |
| 145 | OCHF₂ | NH₂ | 3-NH₂-4-(MeOMe)-1-Pyrd |
| 146 | OCHF₂ | NH₂ | 3-NH₂-4-(CF₃CH₂O)-1-Pyrd |
| 147 | OCF₃ | H | 1-Piz |
| 148 | OCF₃ | H | 3-Me-1-Piz |
| 149 | OCF₃ | H | 3,5-diMe-1-Piz |
| 150 | OCF₃ | H | 2,5-diMe-1-Piz |
| 151 | OCF₃ | H | 3,3-diMe-1-Piz |
| 152 | OCF₃ | H | 4-Me-1-Piz |

TABLE 1-continued

| Cpd No. | R¹ | R³ | R² |
|---|---|---|---|
| 153 | OCF₃ | H | 3,4-diMe-1-Piz |
| 154 | OCF₃ | H | 4-Et-1-Piz |
| 155 | OCF₃ | H | 4-(2-HOEt)-1-Piz |
| 156 | OCF₃ | H | 4-(2-MeOEt)-1-Piz |
| 157 | OCF₃ | H | 4-(2-AcOEt)-1-Piz |
| 158 | OCF₃ | H | 4-(2-NH₂Et)-1-Piz |
| 159 | OCF₃ | H | 4-(4-NH₂Bz)-1-Piz |
| 160 | OCF₃ | H | 4-HCO-1-Piz |
| 161 | OCF₃ | H | 4-Ac-1-Piz |
| 162 | OCF₃ | H | 4-(AcMe)-1-Piz |
| 163 | OCF₃ | H | 4-(HOOCMe)-1-Piz |
| 164 | OCF₃ | H | 4-(EtcMe)-1-Piz |
| 165 | OCF₃ | H | 1-Diz |
| 166 | OCF₃ | H | 4-Me-1-Diz |
| 167 | OCF₃ | H | 3-oxo-1-Piz |
| 168 | OCF₃ | H | 4-Me-3-oxo-1-Piz |
| 169 | OCF₃ | H | 3-HO-1-Azt |
| 170 | OCF₃ | H | 3-HO-1-Pyrd |
| 171 | OCF₃ | H | 3-HO-4-MeO-1-Pyrd |
| 172 | OCF₃ | H | 3,4-diMeO-1-Pyrd |
| 173 | OCF₃ | H | 3-NH₂-1-Azt |
| 174 | OCF₃ | H | 3-NHMe-1-Azt |
| 175 | OCF₃ | H | 3-NHEt-1-Azt |
| 176 | OCF₃ | H | 3-(NH₂Me)-1-Azt |
| 177 | OCF₃ | H | 3-[(NHMe)Me]-1-Azt |
| 178 | OCF₃ | H | 3-[(NMe₂)Me]-1-Azt |
| 179 | OCF₃ | H | 3-NH₂-1-Pyrd |
| 180 | OCF₃ | H | 3-NHMe-1-Pyrd |
| 181 | OCF₃ | H | 3-NMe₂-1-Pyrd |
| 182 | OCF₃ | H | 3-(NH₂Me)-1-Pyrd |
| 183 | OCF₃ | H | 3-[(NHMe)Me]-1-Pyrd |
| 184 | OCF₃ | H | 3-[(NHEt)Me]-1-Pyrd |
| 185 | OCF₃ | H | 3-[(NMe₂)Me]-1-Pyrd |
| 186 | OCF₃ | H | 3-NH₂-4-Me-1-Pyrd |
| 187 | OCF₃ | H | 3-NH₂-4-HO-1-Pyrd |
| 188 | OCF₃ | H | 3-NH₂-4-MeO-1-Pyrd |
| 189 | OCF₃ | H | 3-NH₂-4-EtO-1-Pyrd |
| 190 | OCF₃ | H | 4-NH₂-1-Pip |
| 191 | OCF₃ | H | 4-NHMe-1-Pip |
| 192 | OCF₃ | H | 3-NH₂-1-Pip |
| 193 | OCF₃ | H | 3-NHMe-1-Pip |
| 194 | OCF₃ | H | 3-NMe₂-1-Pip |
| 195 | OCF₃ | H | 3-NH₂-1-Azp |
| 196 | OCF₃ | H | 3-NH₂-3-Me-1-Pyrd |
| 197 | OCF₃ | H | 1-Imid |
| 198 | OCF₃ | H | 4-Me-1-Imid |
| 199 | OCF₃ | H | Mor |
| 200 | OCF₃ | H | Thz |
| 201 | OCH₂F | H | 3,3-diMe-1-Piz |
| 202 | OCH₂F | H | 4-Me-1-Diz |
| 203 | OCH₂F | H | 1-Piz |
| 204 | OCH₂F | H | 1-Diz |
| 205 | OCH₂F | H | 3-NH₂-1-Pyrd |
| 206 | OCH₂F | H | 3-Me-1-Piz |
| 207 | OCH₂F | H | 4-Me-1-Piz |
| 208 | OCH₂F | H | 3-NH₂-4-Me-1-Pyrd |
| 209 | OCH₂F | H | 3,5-diMe-1-Piz |
| 210 | OCH₂F | H | 3,4-diMe-1-Piz |
| 211 | OCH₂F | H | 3-NHMe-1-Pyrd |
| 212 | OCH₂F | H | 3-NMe₂-1-Pyrd |
| 213 | OCF₃ | NH₂ | 1-Piz |
| 214 | OCF₃ | NH₂ | 3-Me-1-Piz |
| 215 | OCF₃ | NH₂ | 3,5-diMe-1-Piz |
| 216 | OCF₃ | NH₂ | 2,5-diMe-1-Piz |
| 217 | OCF₃ | NH₂ | 3,3-diMe-1-Piz- |
| 218 | OCF₃ | NH₂ | 4-Me-1-Piz |
| 219 | OCF₃ | NH₂ | 3,4-diMe-1-Piz |
| 220 | OCF₃ | NH₂ | 4-Et-1-Piz |
| 221 | OCF₃ | NH₂ | 4-(2-HOEt)-1-Piz |
| 222 | OCF₃ | NH₂ | 4-(2-MeOEt)-1-Piz |
| 223 | OCF₃ | NH₂ | 4-(2-AcOEt)-1-Piz |
| 224 | OCF₃ | NH₂ | 4-(2-NH₂Et)-1-Piz |
| 225 | OCF₃ | NH₂ | 4-(4-NH₂Bz)-1-Piz |
| 226 | OCF₃ | NH₂ | 4-HCO-1-Piz |
| 227 | OCF₃ | NH₂ | 4-Ac-1-Piz |
| 228 | OCF₃ | NH₂ | 4-(AcMe)-1-Piz |
| 229 | OCF₃ | NH₂ | 4-(HOOCMe)-1-Piz |
| 230 | OCF₃ | NH₂ | 4-(EtcMe)-1-Piz |
| 231 | OCF₃ | NH₂ | 1-Diz |
| 232 | OCF₃ | NH₂ | 4-Me-1-Diz |
| 233 | OCF₃ | NH₂ | 3-oxo-1-Piz |
| 234 | OCF₃ | NH₂ | 4-Me-3-oxo-1-Piz |
| 235 | OCF₃ | NH₂ | 3-HO-1-Azt |
| 236 | OCF₃ | NH₂ | 3-HO-1-Pyrd |
| 237 | OCF₃ | NH₂ | 3-HO-4-MeO-1-Pyrd |
| 238 | OCF₃ | NH₂ | 3,4-diMeO-1-Pyrd |
| 239 | OCF₃ | NH₂ | 3-NH₂-1-Azt |
| 240 | OCF₃ | NH₂ | 3-NHMe-1-Azt |
| 241 | OCF₃ | NH₂ | 3-NHEt-1-Azt |
| 242 | OCF₃ | NH₂ | 3-[(NH₂)Me]-1-Azt |
| 243 | OCF₃ | NH₂ | 3-(NHMeMe)-1-Azt |
| 244 | OCF₃ | NH₂ | 3-[(NMe₂)Me]-1-Azt |
| 245 | OCF₃ | NH₂ | 3-NH₂-1-Pyrd |
| 246 | OCF₃ | NH₂ | 3-NHMe-1-Pyrd |
| 247 | OCF₃ | NH₂ | 3-NMe₂-1-Pyrd |
| 248 | OCF₃ | NH₂ | 3-[(NH₂)Me]-1-Pyrd |
| 249 | OCF₃ | NH₂ | 3-[(NHMe)Me]-1-Pyrd |
| 250 | OCF₃ | NH₂ | 3-[(NHEt)Me]-1-Pyrd |
| 251 | OCF₃ | NH₂ | 3-[(NMe₂)Me]-1-Pyrd |
| 252 | OCF₃ | NH₂ | 3-NH₂-4-Me-1-Pyrd |
| 253 | OCF₃ | NH₂ | 3-NH₂-4-HO-1-Pyrd |
| 254 | OCF₃ | NH₂ | 3-NH₂-4-MeO-1-Pyrd |
| 255 | OCF₃ | NH₂ | 3-NH₂-4-EtO-1-Pyrd |
| 256 | OCF₃ | NH₂ | 4-NH₂-1-Pip |
| 257 | OCF₃ | NH₂ | 4-NHMe-1-Pip |
| 258 | OCF₃ | NH₂ | 3-NH₂-1-Pip |
| 259 | OCF₃ | NH₂ | 3-NHMe-1-Pip |
| 260 | OCF₃ | NH₂ | 3-NMe₂-1-Pip |
| 261 | OCF₃ | NH₂ | 3-NH₂-1-Azp |
| 262 | OCF₃ | NH₂ | 3-NH₂-3-Me-1-Pyrd |
| 263 | OCF₃ | NH₂ | 1-Imid |
| 264 | OCF₃ | NH₂ | 4-Me-1-Imid |
| 265 | OCF₃ | NH₂ | Mor |
| 266 | OCF₃ | NH₂ | Thz |
| 267 | OCH₂F | NH₂ | 3,3-diMe-1-Piz |
| 268 | OCH₂F | NH₂ | 4-Me-1-Diz |
| 269 | OCH₂F | NH₂ | 1-Piz |
| 270 | OCH₂F | NH₂ | 1-Diz |
| 271 | OCH₂F | NH₂ | 3-NH₂-1-Pyrd |
| 272 | OCH₂F | NH₂ | 3-Me-1-Piz |
| 273 | OCH₂F | NH₂ | 4-Me-1-Piz |
| 274 | OCH₂F | NH₂ | 3-NH₂-4-Me-1-Pyrd |
| 275 | OCH₂F | NH₂ | 3,5-diMe-1-Piz |
| 276 | OCH₂F | NH₂ | 3,4-diMe-1-Piz |
| 277 | OCH₂F | NH₂ | 3-NHMe-1-Pyrd |
| 278 | OCH₂F | NH₂ | 3-NMe₂-1-Pyrd |
| 279 | OCHF₂ | H | 3-(HOMe)-1-Piz |
| 280 | OCHF₂ | NH₂ | 3-(HOMe)-1-Piz |
| 281 | OCHF₂ | H | 4-(SfoMe)-3-Me-1-Piz |
| 282 | OCHF₂ | NH₂ | 4-(SfoMe)-3-Me-1-Piz |
| 283 | OCHF₂ | H | 4-(AcEt)-1-Piz |
| 284 | OCHF₂ | NH₂ | 4-(AcEt)-1-Piz |
| 285 | OCHF₂ | H | 4-(AcEt)-3-Me-1-Piz |
| 286 | OCHF₂ | NH₂ | 4-(AcEt)-3-Me-1-Piz |

| | |
|---|---|
| Ac | acetyl |
| Azp | perhydroazepinyl |
| Azt | azetidinyl |
| Bz | benzyl |
| Diz | perhydro-1,4-diazepinyl (= homopiperazinyl) |
| Et | ethyl |
| Etc | ethoxycarbonyl |
| Imid | imidazolyl |
| Me | methyl |
| Mor | morpholino |
| Pip | piperidyl |
| Piz | piperazinyl |
| iPr | isopropyl |
| Pyrd | pyrrolidinyl |
| Sfo | sulfo |
| Thz | perhydro-1,4-thiazin-4-yl |

TABLE 1-continued

| Cpd No. | R¹ | R³ | R² |
|---|---|---|---|

(= thiomorpholino)

Of the compounds listed above, the following are preferred, that is to say Compounds No. 1, 2, 3, 5, 24, 34, 39, 41, 43, 45, 46, 48, 56, 59, 72, 74, 75, 76, 78, 79, 82, 93, 94, 97, 107, 114, 116, 129, 131, 133, 136, 137, 139, 141, 142, 144, 179, 186, 202, 203, 204, 205, 206, 207, 208, 209, 213, 214, 245, 252, 268, 269, 270, 271, 272, 273, 274, 275, 279, 280, 281, 282, 283, 284, 285 and 286, and the following are the more preferred, that is to say Compounds No. 1, 2, 3, 5, 34, 39, 43, 45, 46, 48, 56, 59, 72, 74, 75, 76, 78, 79, 82, 93, 94, 107, 116, 129, 131, 133, 136, 137, 139, 141, 142, 144, 179 and 284.

The following are the most preferred:
1. 1-Cyclopropyl-8-difluoromethoxy-6-fluoro-7-( 1-piperazinyl)-1,4-dihydro-4-oxoquinoline-3-carboxylic acid;
2. 1-Cyclopropyl-8-difluoromethoxy-6-fluoro-7-( 3-methyl-1-piperazinyl)-1,4-dihydro-4-oxoquinoline-3-carboxylic acid;
3. 1-Cyclopropyl-8-difluoromethoxy-6-fluoro-7-( 3,5-dimethyl-1-piperazinyl)-1,4-dihydro-4-oxoquinoline-3-carboxylic acid;
34. 1-Cyclopropyl-8-difluoromethoxy-6-fluoro-7-( 3-amino-1-pyrrolidinyl) -1,4-dihydro-4-oxoquinoline-3-carboxylic acid;
74. 5-Amino-1-cyclopropyl-8-difluoromethoxy-6-fluoro-7-(1-piperazinyl)-1,4-dihydro-4-oxoquinoline-3-carboxylic acid;
75. 5-Amino-1-cyclopropyl-8-difluoromethoxy-6-fluoro-7-(3-methyl-1-piperazinyl)-1,4-dihydro-4-oxoquinoline-3-carboxylic acid;
76. 5-Amino-1-cyclopropyl-8-difluoromethoxy-6-fluoro-7-(3,5-dimethyl-1-piperazinyl)-1.4-dihydro-4-oxoquinoline- 3-carboxylic acid;
78. 5-Amino-1-cyclopropyl-8-difluoromethoxy-6-fluoro-7-(4-methyl-1-piperazinyl)-1,4-dihydro-4-oxoquinoline-3-carboxylic acid;
93. 5-Amino-1-cyclopropyl-8-difluoromethoxy-6-fluoro-7-(1-homopiperazinyl)-1,4-dihydro-4-oxoquinoline-3-carboxylic acid;
107. 5-Amino-1-cyclopropyl-8-difluoromethoxy-6-fluoro-7-(3-amino-1-pyrrolidinyl)-1,4-dihydro-4-oxoquinoline-3-carboxylic acid;
139. 5-Amino-1-cyclopropyl-8-difluoromethoxy-6-fluoro-7-(3-fluoromethyl-1-piperazinyl)-1,4-dihydro-4-oxoquinoline- 3-carboxylic acid;
144. 5-Amino-1-cyclopropyl-8-difluoromethoxy-6-fluoro-7-(3-methyl-1-homopiperazinyl)-1,4-dihydro-4-oxoquinoline- 3-carboxylic acid.

Also preferred are pharmaceutically acceptable salts, esters and amides, more preferably salts and esters, and most preferably hydrochlorides and methanesulfonates, of the above preferred and most preferred Compounds.

In general terms, the compounds of the present invention may be prepared by reacting a compound of formula (VI):

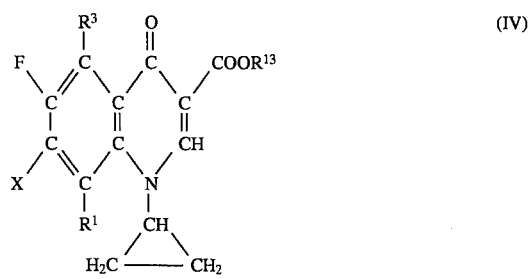

(IV)

(in which $R^1$ and $R^3$ are as defined above; X represents a halogen atom and is preferably a fluorine atom; and $R^{13}$ represents a hydrogen atom or a carboxy-protecting group) or an active derivative or equivalent thereof with a compound of formula (VII):

$$R^2-H \qquad (VII)$$

(in which $R^2$ is as defined above) or an active derivative or equivalent thereof, and, if necessary, subjecting the product to any one or more of the reactions: deprotection, salification, esterification and amidation.

$R^{13}$ may represent any carboxy-protecting group known in organic chemistry for use with this type of compound and may be incorporated into and (if desired) removed from the compound by well known methods which require no elaboration here. However, $R^{13}$ is preferably a hydrogen atom or a $C_1-C_6$, preferably $C_1-C_4$, alkyl group, for example a methyl, ethyl, propyl, isopropyl, butyl, t-butyl, or hexyl group, most preferably a hydrogen atom, a methyl group or an ethyl group.

Alternatively, $R^{13}$ may represent a boron difluoride ($BF_2$) group. In this case, the boron difluoride group will normally form a coordinate bond with the oxygen atom at the 4-position of the quinoline ring.

A preferred method of preparing the compounds of the invention is illustrated in more detail by Reaction Scheme A:

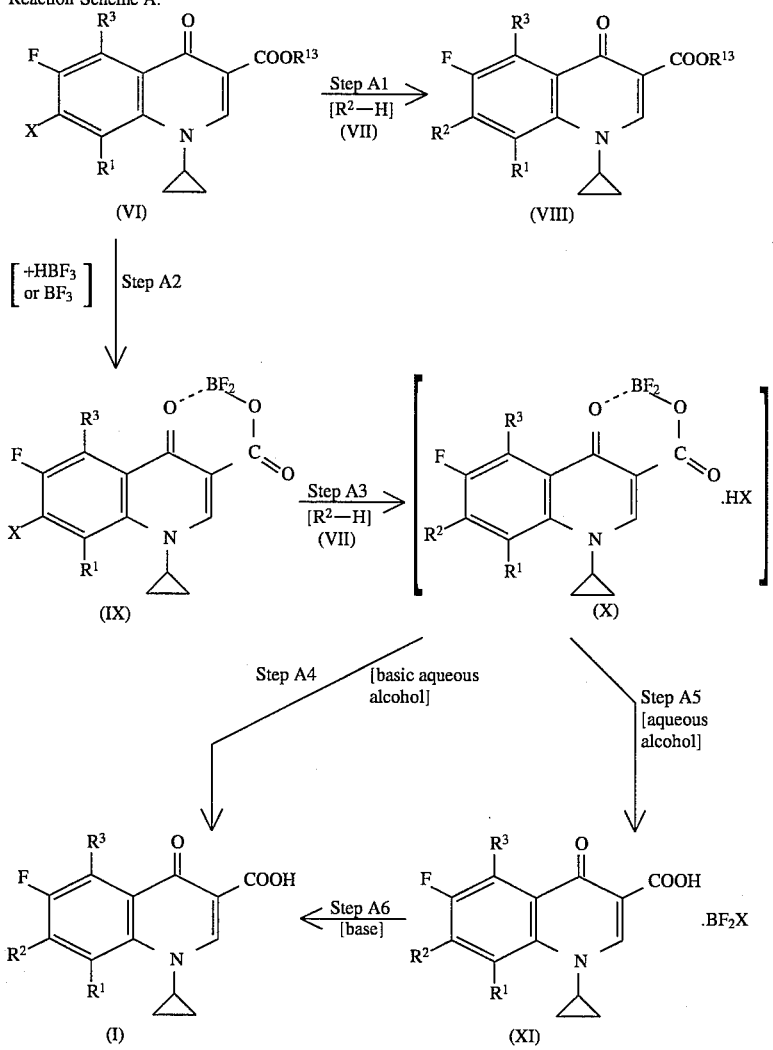

Reaction Scheme A:

In the above formulae, $R^1$, $R^2$, $R^3$, X and $R^{13}$ are as defined above.

In the reactions shown in the above reaction scheme, the compounds of formula (I) of the present invention can be prepared by reacting a compound of formula (VI) or its boron difluoride chelate of formula (IX) with an amine compound of formula (VII) in Steps A1 and A3, respectively. The reaction may be effected in the presence or absence of an acid binding agent and in the presence or absence of a solvent.

The molar ratio of the compound of formula (VI) or (IX) to the amine of formula (VII) is not critical, although we generally prefer to employ equimolar amounts of the two reagents or a molar excess of the amine.

Where a solvent is employed, its nature is not particularly critical, provided that it has no adverse effect on the reaction. Examples of suitable solvents include: aprotic polar solvents, especially sulfoxides, such as dimethyl sulfoxide, or amides, such as dimethylformamide, hexamethylphosphoric triamide or dimethylacetamide; however, other solvents may also be used, including: ketones, such as acetone or methyl ethyl ketone; ethers, such as diethyl ether, tetrahydrofuran or dioxane; esters, such as ethyl acetate; alcohols, such as methanol, ethanol, propanol, isopropanol or butanol; and nitriles, such as acetonitrile. Of these, the aprotic polar solvents are preferred.

Where an acid binding agent is employed, its nature is likewise not particularly critical, provided that it has no adverse effect on the reaction and that it is capable of binding to, and hence effectively removing from the reaction, the acid produced in the course of the reaction. Examples of suitable acid binding agents include: tertiary amines, such as 1,8-diazabicyclo-[5.4.0]-7-undecene, 1,5-diazabicyclo[4.3.0]-5-nonene, triethylamine, tributylamine, pyridine, picoline, lutidine or collidine; and inorganic bases, preferably alkali metal carbonates, such as sodium carbonate or potassium carbonate, or alkali metal alkoxides, such as sodium methoxide, sodium ethoxide or potassium t-butoxide. The amount of acid binding agent employed is preferably equimolar or a molar excess, with respect to the compound of formula (VI) or (IX), more preferably a molar ratio of said compound of formula (VI) or (IX) to said acid binding agent of from 1:1 to 1:5. However, where one of the afore-mentioned amines is used as acid binding agent, it is preferably employed in a large excess, in which case it may serve both as the acid binding agent and as solvent. The reaction may also proceed smoothly even when an acid binding agent is not employed because an excess of the amine of formula (VII) can serve as the acid binding agent.

The reaction may be carried out over a wide range of temperatures, and the exact reaction temperature is not critical to the invention. However, we generally find it convenient to carry out the reaction at a temperature ranging from 0° C. to 200° C.

In the compound of formula (VIII) where $R^{13}$ represents a carboxy-protecting group, this is then removed to prepare the corresponding compound where $R^{13}$ represents a hydrogen atom. This removal may be effected by well known methods appropriate to the nature of the carboxy-protecting group represented by $R^{13}$.

After the reaction is complete, the desired compound of the invention can be recovered from the reaction mixture by treatment in a conventional manner, and, if desired, may be further purified by such conventional techniques as recrystallization or the various chromatography techniques, notably column chromatography.

In the reactions represented by steps A2 to A6, a chelate of formula (X) of the desired compound is obtained first, and this is then converted into the $BF_2X$ addition product (XI) of the compound of formula (I) or the compound of formula (I) itself by treatment with an aqueous alcohol or a basic aqueous alcohol. The $BF_2X$ addition product (XI) of the compound of formula (I) is easily converted into the compound (I) itself by treatment with a base.

Examples of bases which may be employed include: alkali metal hydroxides, such as sodium hydroxide or potassium hydroxide; alkali metal carbonates, such as sodium carbonate or potassium carbonate; alkali metal alkoxides, such as sodium methoxide, sodium ethoxide or potassium t-butoxide; and tertiary amines, such as 1,8-diazabicyclo [5.4.0]-7-undecene, 1,5-diazabicyclo-[4.3.0]-5-nonene, triethylamine or 4-dimethylaminopyridine.

The compound of formula (I) or its $BF_2X$ addition product (XI) may, if desired, be converted into a desired salt by conventional means.

Conversion of the compound of formula (VI) to the boron difluoride chelate of formula (IX) can be carried out, for example, by reaction with hydrofluoroboric acid or boron trifluoride by the method described in Japanese Patent Application Kokai (i.e. as laid open to public inspection) No. 67290/84.

The compound of formula (I) thus prepared may exist as a mixture of optical isomers due to the presence of an asymmetric carbon atom in the moiety of the compound represented by $R^2$ or as geometric (cis or trans) isomers due to, for example, the presence of two or more substituents on the heterocyclic group represented by $R^2$. In such a case, individual isomers of the compound may be prepared, if desired, by using as the starting material of formula $R^2$—H (VII) a compound which has been optically resolved or separated in advance to obtain the corresponding optical or geometric isomer of the desired compound (I). Alternatively, a mixture of optical or geometric isomers of the compound (I) may be prepared, and these may be resolved or separated into the individual isomers by conventional techniques.

The compounds of formula (VI) used as starting materials in the afore-mentioned reactions can be prepared, for instance, by the following Reaction Scheme B.

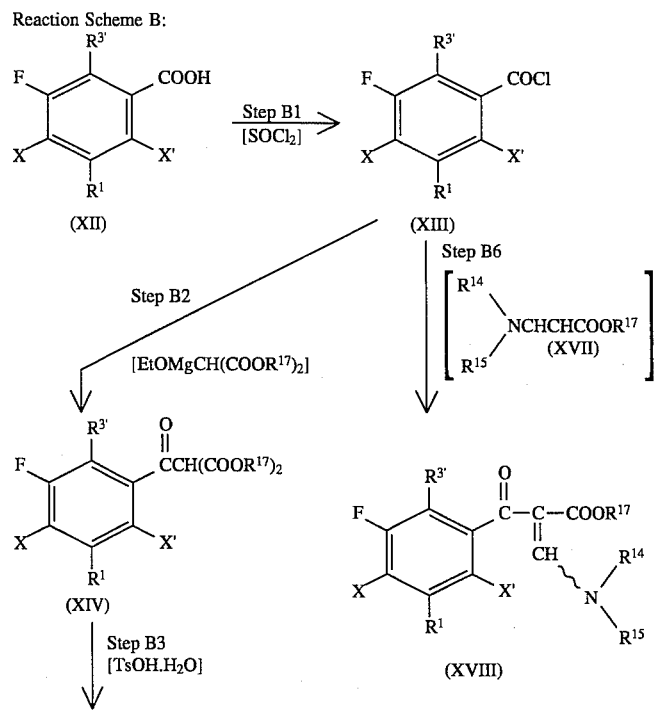

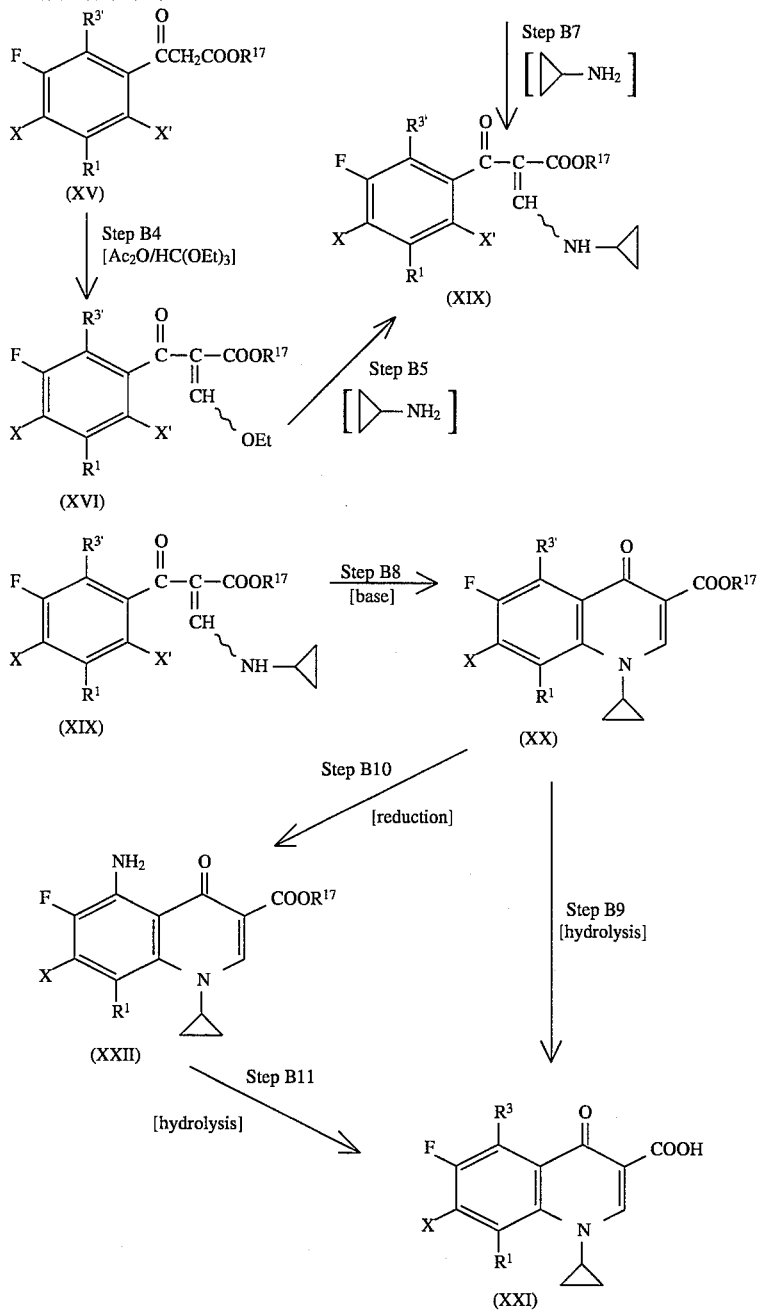

Reaction Scheme B:

In the above formulae:

$R^1$, $R^3$ and X are as defined above;

$R^{3'}$ represents hydrogen atom or a nitro ($NO_2$) group;

$R^{17}$ represents a carboxy-protecting group, as illustrated in relation to the groups which may be represented by $R^{13}$;

X' represents a halogen atom, such as a fluorine, chlorine, bromine or iodine group;

$R^{14}$ and $R^{15}$ are the same or different and each represents a $C_1$–$C_6$ alkyl group, for example as exemplified above in relation to the alkyl groups which may be represented by $R^4$, or $R^{14}$ and $R^{15}$ may, together with the nitrogen atom to which they are attached form a heterocyclic group having from 5 to 6 ring atoms of which 0 or 1 is an additional hetero-atom selected from the group consisting of nitrogen, oxygen and sulfur hereto-atoms and which is unsubstituted or as one or two oxo substituents on a sulfur hetero-atom to form a sulfinyl or sulfonyl group;

Ac represents the acetyl group;

Et represents the ethyl group; and

Ts represents the p-tosyl (p-toluenesulfonyl) group.

The reaction conditions and treatment after completion of the reaction in each Step are described in more detail in the following Preparations. Of course, the details of reaction conditions etc given in these Preparations are merely by way of example and it will be appreciated that these well known reactions may be conducted in a variety of different ways.

In Step B8, examples of suitable bases include: alkali metal hydrides, such as sodium hydride or potassium hydride; alkali metal carbonates, such as sodium carbonate or potassium carbonate; and alkali metal alkoxides, such as sodium methoxide or potassium t-butoxide.

reduced to the corresponding amino compound; after which the products may be treated as shown also in Reaction Scheme B':

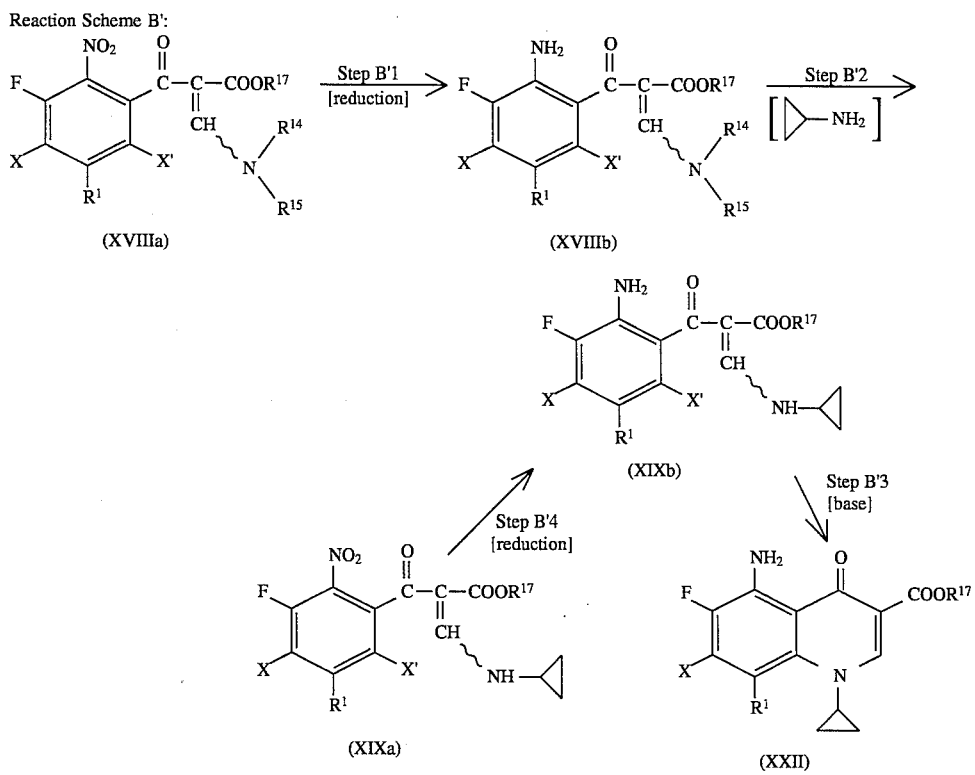

In the compound of formula (XX), where $R^{3'}$ represents a hydrogen atom, the compound may be the desired compound of formula (VI) or it may be hydrolised in Step B9 to give the free acid of formula (XXI). However, where $R^{3'}$ represents a nitro group, it is necessary that this should be reduced to an amino group and form the compound of formula (XXII); this may be the desired compound or it may likewise be hydrolised to give the compound of formula (XXI).

Where $R^{3'}$ in the compound of formula (XII) used as the starting material in this Reaction Scheme represents a nitro group, this compound may be prepared by nitration of the corresponding Compound where $R^{3'}$ represents a hydrogen atom, e.g. as shown below:

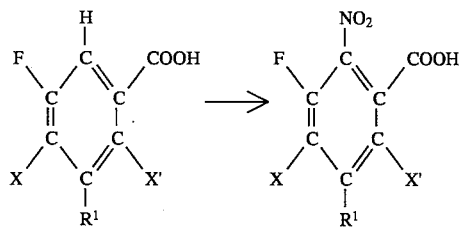

As an alternative to Steps B8, B10 and B11, where $R^{3'}$ represents a nitro group, the compound of formula (XIX) [shown in the following Scheme as formula (XIXa)] may be reduced to give the amino compound; also the compound of formula (XVIII) where $R^{3'}$ represents a nitro group [shown in the following Scheme as formula (XVIIIa)] may be In the above formulae, $R^1$, $R^{14}$, $R^{15}$, $R^{17}$, X and X' are as defined above.

Those compounds of formula (XII) in which $R^{3'}$ represents a hydrogen atom and $R^1$ represents a difluoromethoxy group can be prepared as shown in Reaction Scheme C, whilst those in which $R^{3'}$ represents a hydrogen atom and $R^1$ represents a trifluoromethoxy group can be prepared as shown in Reaction Scheme D:

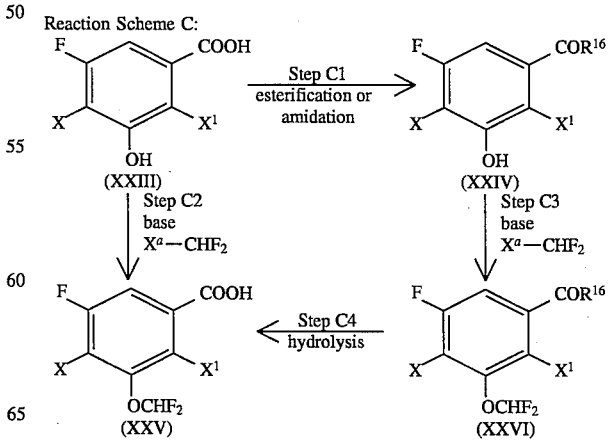

Reaction Scheme O:

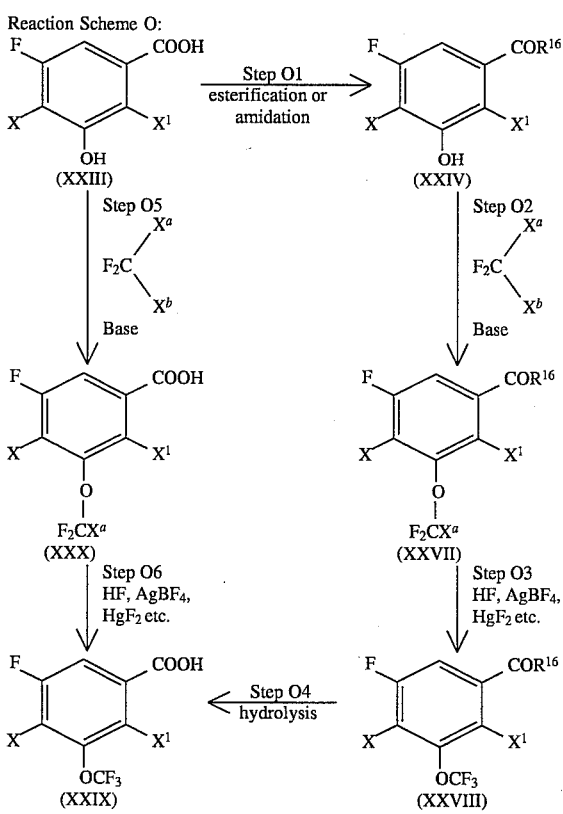

In the above formulae, X and X' are as defined above, $R^{16}$ represents a $C_1$–$C_6$ alkoxy group or an amino group; and $X^a$ and $X^b$ are the same or different and each represents a halogen atom, for example a chlorine, bromine or iodine atom, but not a fluorine atom.

In Reaction Scheme C, by replacing the compound of formula $X^a$—$CHF_2$ by a compound of formula $X^a$—$CHF_2$, the corresponding compounds having a monofluoromethoxy group at the 3-position can be prepared.

2,4,5-Trifluoro-3-hydroxybenzoic acid, and the corresponding compounds having other halogen atoms at the 2- and 4- positions, which may be employed as the starting materials in these Reaction Schemes, can be prepared by the decarboxylation by heating of the known compound, 3,5,6-trifluoro-4-hydroxyphthalic acid, or the corresponding compounds having other halogen atoms at the 3- and 5- positions, in an aqueous medium, e.g. water or an aqueous solvent, as shown below:

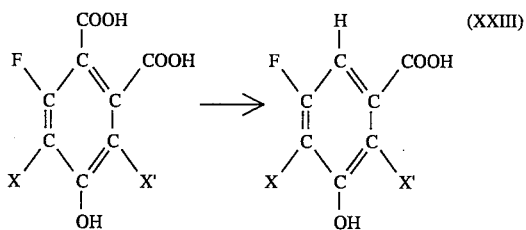

The compounds of the invention possess a powerful antibacterial activity. Estimation by the agar plate dilution method showed an excellent growth inhibitory effect against a wide range of pathogenic bacteria, including Gram-positive bacteria such as *Staphylococcus aureus* or *Enterococcus* species, and Gram-negative bacteria such as *Escherichia coli*, dysentery bacillus, Shigella, *Klebsiella pneumoniae*, Myxomycetes, Serratia, Enterobacter, Salmonella or *Pseudomonas aeruginosa*, including normally resistant strains thereof.

The compounds of the invention can be administered as conventional pharmaceutical formulations, depending upon the intended route of administration. For example, for oral administration, they may be formulated as powders, granules, tablets, capsules, syrups or similar orally administerable formulations, which can be produced by mixing the active compound with carriers, excipients or diluting agents, such as glucose, sucrose, lactose, sorbitol, starch, polyvinylpyrrolidone, mannitol, calcium carbonate, calcium phosphate, sodium chloride or boric acid. For parenteral administration, they may be formulated as conventional injections suitable for, for example, intravenous or intramuscular injection. The dose will vary, depending upon the nature of the disorder, the route of administration, and the symptoms, age and body weight of the patient; however, for an adult human patient, a suitable dose for oral administration would be from 100 mg to 1000 mg per day, which could be given in a single dose or in divided doses.

The invention is further illustrated by the following Examples, which illustrate the preparation of various of the compounds of the invention. The preparation of certain of the starting materials employed in these Examples is illustrated in the Preparations. The activity of certain of the compounds of the invention is illustrated by the subsequent Biological Activity data.

PREPARATION 1

3-Difluoromethoxy-2,4,5-trifluorobenzoic acid [(XXV), X=X'=F] (ester route)

1(a) Ethyl 2,4,5-trifluoro-3-hydroxybenzoate [(XXIV), X=X'=F, $R^{16}$=$C_2H_5O$]

5 ml of concentrated sulfuric acid were added to a solution of 20.0 g (0.104 moles) of 2,4,5-trifluoro-3-hydroxybenzoic acid [(XXIII), X=X'=F] (prepared as described in Preparation 13) in 500 ml of ethanol, and the mixture was heated under reflux for 4 hours. The ethanol was then removed by distillation under reduced pressure, and the residue was extracted with ethyl acetate. The extract was washed with a saturated aqueous solution of sodium bicarbonate and with water, in that order, after which it was dried over anhydrous sodium sulfate and then concentrated by evaporation under reduced pressure, to give 16.9 g of ethyl 2,4,5-trifluoro-3-hydroxybenzoate as a colorless powder.

Mass Spectrum (CI): m/e 221 ($M^+$+1), 175 ($M^+$—$OC_2H_5$) ("CI" means "chemical ionization").

1(b) Ethyl 3-difluoromethoxy-2,4,5-trifluorobenzoate [(XXVI), X=X'=F, $R^{16}$=$C_2H_5O$]

1.76 g (0.044 moles) of a 60% w/w suspension of sodium hydride in mineral oil was added in small portions, whilst stirring and ice-cooling, to a solution of 8.83 g (0.04 moles) of ethyl 2,4,5-trifluoro-3-hydroxybenzoate [(XXIV), X=X'=F, $R^{16}$=$C_2H_5O$] [prepared as described in step (a) above] in 40 ml of dimethylformamide and, after the addition was complete, the mixture was stirred, whilst ice-cooling, for an additional 30 minutes. At the end of this time, the reaction mixture was transferred into a 200 ml stainless steel autoclave, and then 100 ml of dimethylformamide containing 28.0 g (0.32 moles) of chlorodifluoromethane were added thereto, and the mixture was stirred under pressure at 95°–100° C. for 5 hours. At the end of this time, the dimethylformamide was removed by distillation under reduced pressure, and water was added to the residue, which was extracted with toluene. The extract was washed with water and dried over anhydrous sodium sulfate, and then the solvent was removed by evaporation under reduced pressure. The residue was subjected to silica gel column chromatography, using toluene as the eluent, to give 4.85 g of ethyl 3-difluoromethoxy-2,4,5-trifluorobenzoate as a colorless liquid.

Mass Spectrum (CI): m/e 271 (M$^+$+1), 225 (M$^+$—OC$_2$H$_5$).

1(c) 3-Difluoromethoxy-2,4,5-trifluorobenzoic acid [(XXV), X=X'=F]

20 ml of a 6% w/v aqueous solution of sodium hydroxide were added to a solution of 5.79 g (0.021 moles) of ethyl 3-difluoromethoxy-2,4,5-trifluorobenzoate [(XXVI), X=X'=F, R$^{16}$=C$_2$H$_5$O] [prepared as described in step (b) above] in 40 ml of ethanol, and the mixture was left at room temperature overnight. The reaction mixture was then acidified by the addition of 3.5 ml of concentrated aqueous hydrochloric acid, and, after concentration by evaporation under reduced pressure, it was extracted with ethyl acetate. The extract was washed with water and dried over anhydrous sodium sulfate, and then the solvent was removed by distillation under reduced pressure, to give 5.22 g of 3-difluoromethoxy-2,4,5-trifluorobenzoic acid as a colorless powder, melting at 68°–70° C.

Mass Spectrum (CI): m/e 243 (M$^+$+1), 225 (M$^+$—OH), 223 (M$^+$—F), 192 (M$^+$—CF$_2$), 175 (M$^+$—CF$_2$—OH).

Nuclear Magnetic Resonance Spectrum (CDCl$_3$, δ ppm): 6.67 (1H, triplet, J=72 Hz); 7.83 (1H, multiplet); 10.74 (1H, broad).

PREPARATION 2

3-Difluoromethoxy-2,4,5-trifluorobenzoic acid [(XXV), X=X'=F] (amide route)

2(a) 2,4,5-Trifluoro-3-hydroxybenzoyl amide [(XXIV), X=X'=F, R$^{16}$=NH$_2$]

300 ml of thionyl chloride were added to a solution of 100.0 g (0.52 moles) of 2,4,5-trifluoro-3-hydroxybenzoic acid [(XXIII), X=X'=F] (prepared as described in Preparation 13) in 400 ml of benzene, and the mixture was heated under reflux for 3 hours. At the end of this time, the solvent and excess thionyl chloride were removed by distillation under reduced pressure, to give 2,4,5-trifluoro-3-hydroxybenzoyl chloride. The whole of this chloride was added dropwise to 1500 ml of 28% w/v aqueous ammonia, whilst stirring and ice-cooling, and the mixture was then stirred for a further 2 hours. At the end of this time, the mixture was allowed to stand at room temperature overnight, after which it was acidified by the addition of dilute aqueous hydrochloric acid. The reaction mixture was then extracted with ethyl acetate, and the extract was washed with water and dried over anhydrous sodium sulfate. The solvent was then removed by distillation under reduced pressure, to give 88.2 g of 2,4,5-trifluoro-3-hydroxybenzoyl amide as a colorless powder, melting at 153°–155° C.

Mass Spectrum (CI): m/e 192 (M$^+$+1), 175 (M$^+$—NH2).

2(b) 3-Difluoromethoxy-2,4,5-trifluorobenzoyl amide [(XXVI), X=X'=F, R$^{16}$=NH$_2$]

5.00 g (0.026 moles) of 2,4,5-trifluoro-3-hydroxybenzoyl amide [(XXIV), X=X'=F, R$^{16}$=NH$_2$] [prepared as described in step (a) above] were dissolved in 130 ml of dimethylformamide. 4.70 g (0.034 moles) of potassium carbonate and 6.8 g (0.079 moles) of chlorodifluoromethane were then added to the resulting solution, and the mixture was stirred in an autoclave at 100° C. for 3 hours. At the end of this time, 500 ml of water were added to the reaction mixture, which was then extracted with ethyl acetate. The extract was washed with water, and the solvent was removed by evaporation under reduced pressure. The residue was subjected to silica gel column chromatography, using a 1:1 by volume mixture of toluene and ethyl acetate as the eluent, to give 5.08 g of 3-difluoromethoxy-2,4,5-trifluorobenzoyl amide as colorless needles, melting at 102°–104° C.

Mass Spectrum (CI): m/e 242 (M$^+$+1), 225 (M$^+$—NH$_2$).

2(c) 3-Difluoromethoxy-2,4,5-trifluorobenzoic acid [(XXV), X=X'=F]

30 ml of an aqueous solution containing 6.60 g (0.096 moles) of sodium nitrite were slowly added dropwise, whilst stirring and ice-cooling, to a suspension of 15.53 g (0.064 moles) of 3-difluoromethoxy- 2,4,5-trifluorobenzoyl amide [(XXVI), X=X'F, R$^{16}$—NH$_2$] [prepared as described in step (b) above] in 20 ml of concentrated aqueous sulfuric acid, and the mixture was heated under reflux for 30 minutes. At the end of this time, it was cooled to room temperature, and then 50 ml of water were added it. The reaction mixture was then extracted with chloroform. The extract was washed with water and dried over anhydrous sodium sulfate, and then the solvent was removed by distillation under reduced pressure, to give 15.59 g of 3-difluoromethoxy-2,4,5-trifluorobenzoic acid as a colorless powder.

This compound had the same melting point, mass spectrum and nuclear magnetic resonance spectrum data as that obtained through the ester route in Preparation 1.

PREPARATION 3

3-Difluoromethoxy-2,4,5-trifluorobenzoic acid [(XXV), X=X'=F] (direct method)

20 ml of dimethylformamide, followed by 4.97 g (0.026 mole) of 2.4,5-trifluoro-3-hydroxybenzoic acid [(XXIII), X=X'=F], were added in portions, whilst ice-cooling, to a solution of 2.18 g (0.052 mole) of sodium hydroxide in 5 ml of water. Thereafter the solution was stirred for 30 minutes, whilst ice-cooling. The reaction mixture was then transferred to a 200 ml stainless steel autoclave, and 100 ml of dimethylformamide containing 24.0 g (0.277 mole) of chlorodifluoromethane were added to it. The mixture was then stirred at between 100° and 110° C. for 5 hours under pressure. At the end of this time, the reaction mixture was poured into water and extracted with chloroform. The chloroform extracts were washed with water and dried over anhydrous sodium sulfate; the solvent was then removed by evaporation under reduced pressure. The residue was purified by column chromatography through silica gel using a 9:1 by volume mixture of ethyl acetate and ethanol as the eluent, to afford 2.00 g of 3-difluoromethoxy-2,4,5-trifluorobenzoic acid as a colorless powder.

This compound had the same melting point, mass spectrum and nuclear magnetic resonance spectrum data as that obtained through the ester route in Preparation 1.

PREPARATION 4

2,4,5-Trifluoro-3-trifluoromethoxybenzoic acid [(XXIX), X=X'=F]

4(a) Ethyl 3-bromodifluoromethoxy-2,4,5-trifluorobenzoate [(XXVII), X=X'=F, X$^a$=Br, R$^{16}$=C$_2$H$_5$O]

1.0 g (0.025 moles) of a 60% w/w suspension of sodium hydride in mineral oil was added in small portions, whilst stirring and ice-cooling, to a solution of 5.0 g (0.023 moles) of ethyl 2,4,5-trifluoro-3-hydroxybenzoate [(XXIV), X=X'=F, R$^{16}$=C$_2$H$_5$O ] [prepared as described in Preparation 1(a)] in 20 ml of dimethylformamide and, after completion of the addition, the mixture was stirred, whilst ice-cooling, for an additional 30 minutes. After this, 30 ml of dimethylformamide containing 28.0 g (0.13 moles) of dibromodifluoromethane were added, and the mixture was stirred at room temperature for 23 hours. At the end of this time, the reaction mixture was poured into 300 ml of water, and extracted with toluene. The extract was washed with water and dried over anhydrous sodium sulfate, and then the solvent was removed by distillation under reduced pressure. The residue was subjected to silica gel column chromatography, using toluene as the eluent, to give 5.60 g of ethyl 3-bromodifluoromethoxy-2,4,5-trifluorobenzoate as a colorless liquid.

Mass Spectrum (CI): m/e 351 ($M^+$+3), 349, ($M^+$+1).

4(b) Ethyl 2,4,5-trifluoro-3-trifluoromethoxybenzoate [(XXVIII), X=X'=F, $R^{16}$=$C_2H_5O$]

1.50 g (0.0043 moles) of ethyl 3-bromodifluoromethoxy-2,4,5-trifluorobenzoate [(XXVII), X=X'=F, $X^a$=Br, $R^{16}$=$C_2H_5O$] [prepared as described in step (a) above] was dissolved in 10 ml of toluene, and 2.50 g (0.013 moles) of silver tetrafluoroborate were added thereto. The mixture was then heated under reflux for 8 hours in the dark, whilst stirring. At the end of this time, the reaction mixture was filtered, and the filtrate was washed with water, dried over anhydrous sodium sulfate, and concentrated by evaporation under reduced pressure. The residue was subjected to silica gel column chromatography, using toluene as the eluent, to give 1.12 g of ethyl 2,4,5-trifluoro-3-trifluoromethoxybenzoate as a colorless liquid.

Mass Spectrum (CI): m/e 289 ($M^+$+1), 269 ($M^+$—F).

4(c) 2,4,5-Trifluoro-3-trifluoromethoxybenzoic acid [(XXIX), X=X'=F]

19.3 ml (0.0193 moles) of a 1N aqueous solution of sodium hydroxide were added t9 a solution of 5.05 g (0.0175 moles) of ethyl 2,4,5-trifluoro-3-trifluoromethoxybenzoate [(XXVIII), X=X'=F, $R^{16}$=$C_2H_5O$] [prepared as described in step (b) above] in 100 ml of ethanol, and the mixture was allowed to stand at room temperature for 2 hours. At the end of this time, 19.3 ml of 1N aqueous hydrochloric acid were added, and then the reaction mixture was concentrated by evaporation under reduced pressure. The residue was then extracted with ethyl acetate. The extract was washed with water, dried over anhydrous sodium sulfate, and evaporated to dryness under reduced pressure, to give 3.98 g of 2,4,5-trifluoro-3-trifluoromethoxybenzoic acid as a colorless powder.

Mass Spectrum (CI): m/e 261 ($M^+$+1), 243 ($M^+$—OH).

Nuclear Magnetic Resonance Spectrum (CDCl$_3$, δ ppm): 7.88 (1H, multiplier).

PREPARATION 5

3-Difluoromethoxy-2,4,5-trifluoro-6-nitrobenzoic acid [(XII), $R^1$=—OCHF$_2$, $R^{3'}$=NO$_2$, X=X'=F]

20 ml of concentrated aqueous nitric acid (d=1.42) were added dropwise, whilst stirring and cooling with water, to a solution of 15.0 g (0.062 moles) of 3-difluoromethoxy-2,4, 5-trifluorobenzoic acid [(XXV), X=X'=F] (prepared as described in Preparation 1, 2 or 3) in 40 ml of concentrated aqueous sulfuric acid, and the mixture was stirred at 60° C. for 7 hours. At the end of this time, it was allowed to stand to cool to room temperature, and then the reaction mixture was poured into ice-water, and extracted with diethyl ether. The extract was washed with a saturated aqueous solution of sodium chloride and dried over anhydrous sodium sulfate; the solvent was then removed by evaporation under reduced pressure, to give 16.6 g of 3-difluoromethoxy-2,4,5-trifluoro-6-nitrobenzoic acid as a yellow powder, melting at 77°–80° C.

Mass Spectrum: m/e 287 ($M^+$), 243 ($M^+$—CO$_2$).

PREPARATION 6

Ethyl 1-cyclopropyl-8-difluoromethoxy-6,7-difluoro-1,4-dihydro-4-oxoquinoline-3-carboxylate [(XX), $R^1$=—OCHF$_2$, $R^{3'}$=H, $R^{17}$=$C_2H_5$, X=F]

6(a) Diethyl 3-difluoromethoxy-2,4,5-trifluorobenzoylmalonate [(XIV), $R^1$=—OCHF$_2$, =$R^{3'}$=H, $R^{17}$=$C_2H_5$, X=X'=F]

15 ml of thionyl chloride were added to a solution of 5.22 g (0.0216 moles) of 3-difluoromethoxy-2,4,5-trifluorobenzoic acid [(XII), $R^1$—OCHF$_2$, $R^{3'}$=H, X=X'=F] (prepared as described in Preparation 1, 2 or 3) in 300 ml of benzene, and the mixture was heated under reflux for 3 hours. At the end of this time, benzene and excess thionyl chloride were removed by distillation under reduced pressure, to give 3-difluoromethoxy-2,4,5-trifluorobenzoyl chloride [(XIII), $R^1$=—OCHF$_2$, $R^{3'}$=H, X=X'=F].

Meanwhile, a suspension of diethyl ethoxymagnesium malonate in diethyl ether was prepared from a mixture of 2.80 g (0.0238 moles) of magnesium ethoxide and 3.81 g (0.0238 moles) of diethyl malonate in 60 ml of anhydrous diethyl ether by heating under reflux for 1 hour, whilst stirring. A solution of the 3-difluoromethoxy-2,4,5-trifluorobenzoyl chloride prepared as described above in 50 ml of anhydrous diethyl ether was then added dropwise to the suspension, whilst stirring at room temperature, and the mixture was then stirred at room temperature for an additional 2 hours. 35 ml of 1N aqueous hydrochloric acid were added to the reaction mixture, and the mixture was vigorously stirred. The organic layer was then separated, washed with water and dried over anhydrous sodium sulfate. The solvent was then removed by evaporation under reduced pressure to give 7.07 g of diethyl 3-difluoromethoxy-2,4,5-trifluorobenzoylmalonate [(XIV), $R^1$=—OCHF$_2$, $R^{3'}$=H, $R^{17}$=$C_2H_5$, X=X'=F] as a brown liquid.

Mass Spectrum (CI): m/e 385 ($M^+$+1), 339 ($M^+$—OC$_2$H$_5$).

6(b) Ethyl 3-difluoromethoxy-2,4,5-trifluorobenzoylacetate [(XV), $R^1$=—OCHF$_2$, $R^{3'}$=H, $R^{17}$=$C_2H_5$, X=X'=F].

The whole of the diethyl-3-difluoromethoxy-2,4,5trifluorobenzoylmalonate [(XIV), $R^1$=—OCHF$_2$, $R^{3'}$=H, $R^{17}$=$C_2H_5$, X=X'=F] [prepared as described in step (a) above] was dissolved in 200 ml of dioxane, and then 4.52 g (0.0238 moles) of p-toluenesulfonic acid monohydrate were added to the resulting solution. The mixture was then heated under reflux for 6 hours. At the end of this time, the reaction mixture was concentrated by evaporation under reduced pressure. 100 ml of water and 2.52 g (0.03 moles) of sodium bicarbonate were added to the residue, and the mixture was extracted with ethyl acetate. The extract was washed with water and dried over anhydrous sodium sulfate, and the solvent was removed by distillation under reduced pressure to give 5.66 g of ethyl 3-difluoromethoxy-2,4,5-trifluorobenzoylacetate as a reddish brown liquid.

Mass Spectrum (CI): m/e 313 ($M^+$+1), 225 ($M^+$—CH$_2$COOC$_2$H$_5$).

6(c) Ethyl 3-cyclopropylamino-2-(3-difluoromethoxy-2,4,5-trifluorobenzoyl)acrylate [(XIX), $R^1$=—OCHF$_2$, $R^{3'}$=H, $R^{17}$=, C$_2$H$_5$, X=X'=F]

20 ml of acetic anhydride and 6 ml of ethyl orthoformate were added to the whole of the ethyl 3-difluoromethoxy-2, 4,5-trifluorobenzoylacetate [(XV), $R^1$=—OCHF$_2$, $R^{3'}$=H, $R^{17}$=$C_2H_5$, X=X'=F] prepared as described in step (b) above, and, after the mixture had been heated under reflux for 2 hours, the excess acetic anhydride and ethyl orthoformate were removed by evaporation under reduced pressure. The residue was dissolved in 200 ml of methylene chloride, and 1.25 g (0.022 moles) of cyclopropylamine was added dropwise, whilst stirring and ice-cooling; the stirring was continued, whilst ice-cooling, for an additional 1 hour. At the end of this time, the reaction mixture was concentrated by evaporation under reduced pressure, and the residue was subjected to silica gel column chromatography, using a 9:1 by volume mixture of toluene and ethyl acetate as the eluent, to give 3.29 g of ethyl 3-cyclopropylamino-2-(3-difluoromethoxy-2,4,5trifluorobenzoyl)acrylate as an amber colored liquid.

Mass Spectrum (CI): m/e 380 ($M^+$+1), 225 [$M^+$—cPr—NH=CH=C(COOEt)].

6(d) Ethyl 1-cyclopropyl-8-difluoromethoxy-6,7-difluoro-1,4-dihydro-4-oxoquinoline-3-carboxylate [(XX), $R^1$=—$OCHF_2$, $R^{3'}$=H, $R^{17}$=$C_2H_5$, X=F]

The whole of the ethyl 3-cyclopropylamino-2-(3-difluoromethoxy-2,4,5-trifluorobenzoyl)acrylate [(XIX), $R^1$=—$OCHF_2$, $R^{3'}$=H, $R^{17}$=$C_2H_5$, X =X'=F] [prepared as described in step (c) above] was dissolved in 150 ml of anhydrous diethyl ether, and then 0.39 g (0.0098 moles) of a 60% w/w suspension of sodium hydride in mineral oil was added in portions, whilst stirring at room temperature to the resulting solution. After completion of the addition, the stirring was continued at room temperature for an additional 1 hour, and then the mixture was acidified by the addition of 1N aqueous hydrochloric acid with vigorous stirring. The reaction mixture was filtered and washed with water and with diethyl ether, in that order, to give 1.44 g of ethyl 1-cyclopropyl-8-difluoromethoxy- 6,7-difluoro-1,4-dihydro-4-oxoquinoline-3-carboxylate as colorless needles, melting at 224°–226° C.

Mass Spectrum (CI): m/e 360 ($M^+$+1).

PREPARATION 7

1-Cyclopropyl-8-difluoromethoxy-6,7-difluoro-1,4-dihydro-4-oxoquinoline-3-carboxylic acid [(XXI), $R^1$=—$OCHF_2$, $R^3$=H, X=F]

9 ml of acetic acid, 1.2 ml of concentrated sulfuric acid and 7 ml of water were added to 1.40 g (0.0039 moles) of ethyl 1-cyclopropyl-8-difluoromethoxy-6,7-difluoro-1,4-dihydro-4-oxoquinoline-3-carboxylate [(XX), $R^1$=—$OCHF_2$, $R^{3'}$=H, $R^{17}$=, $C_2H_5$, X=F] (prepared as described in Preparation 6), and the mixture was heated under reflux for 1 hour. At the end of this time, it was cooled to room temperature and poured into ice-water. The precipitated crystals were collected by filtration and washed with water and with diethyl ether, in that order, to give 1.09 g of 1-cyclopropyl-8-difluoromethoxy-6,7-difluoro-1,4-dihydro-4-oxoquinoline- 3-carboxylic acid as colorless needles, melting at 202°–207° C.

Mass Spectrum (CI): m/e 332 ($M^+$+1).

Elemental analysis: Calculated for $C_{14}H_9F_4NO_4$: C, 50.77%; H, 2.74%; N, 4.23%. Found: C, 50.53%; H; 2.79%; N, 4.06%.

PREPARATION 8

1-Cyclopropyl-8-difluoromethoxy-6,7-difluoro-1,4-dihydro-4-oxoquinoline-3-carboxylic acid boron difluoride chelate [(IX), $R^1$=—$OCHF_2$, $R^3$=H, X=F]

5.63 g of boron trifluoride diethyl etherate were added to a solution of 9.50 g (0.0265 moles) of ethyl 1- cyclopropyl-8-difluoromethoxy-6,7-difluoro-1,4-dihydro-4-oxoquinoline- 3-carboxylate [(VI), $R^1$=—$OCHF_2$, $R^3$=H, $R^{13}$=$C_2H_5$, X=F] (prepared as described in Preparation 6) in 150 ml of methyl isobutyl ketone, and the mixture was heated under reflux for 6 hours. At the end of this time, the reaction mixture was cooled with ice, and the precipitated crystals were collected by filtration and washed with diethyl ether and with chloroform, in that order, to give 6.15 g of 1-cyclopropyl- 8-difluoromethoxy-6,7-difluoro-1,4-dihydro-4-oxoquinoline- 3-carboxylic acid boron difluoride chelate as a colorless powder, melting at 225°–233° C.

Mass Spectrum (CI): m/e 380 ($M^+$+1).

Elemental analysis: Calculated for $C_{14}H_8BF_6NO_4 \cdot \frac{1}{2}H_2O$: C, 43.33%; H, 2.34%; N, 3.61%. Found: C, 43.06%; H, 2.09%; N, 3.78%.

PREPARATION 9

Ethyl 1-cyclopropyl-6,7-difluoro-8-trifluoromethoxy-1,4-dihydro- 4-oxoquinoline-3-carboxylate [(VI), $R^1$=—$OCF_3$, $R^3$=H, $R^{13}$=$C_2H_5$, X=F]

Following a procedure similar to that described in Preparation 6, but using 6.02 g of 2,4,5-trifluoro-3-trifluoromethoxybenzoic acid (prepared as described in Preparation 4) [(XXIX), X=X'=F], 2.41 g of ethyl 1-cyclopropyl-6,7-difluoro-8-trifluoromethoxy-1,4-dihydro-4-oxoquinoline-3-carboxylate were obtained as colorless needles, melting at 160°–161° C.

Mass Spectrum (CI): m/e 378 ($M^+$+1).

PREPARATION 10

1-Cyclopropyl-6,7-difluoro-8-trifluoromethoxy-1,4-dihydro- 4-oxoquinoline-3-carboxylic acid boron difluoride chelate [(IX), $R^1$=—$OCF_3$, $R^3$=H, X=F]

Following a procedure similar to that described in Preparation 8, but using 2.10 g of ethyl 1-cyclopropyl -6,7-difluoro-8-trifluoromethoxy-1,4-dihydro-4-oxoquinoline-3-carboxylate [(VI), $R^1$=—$OCF_3$, $R^3$=H, $R^{13}$=$C_2H_5$, X=F] (prepared as described in Preparation 9), 1.82 g of 1-cyclopropyl-6,7-difluoro-8-trifluoromethoxy-1,4-dihydro-4-oxoquinoline-3-carboxylic acid boron difluoride chelate were prepared as a colorless powder, melting at 266°–271° C.

Mass Spectrum (CI): m/e 398 ($M^+$+1).

Elemental analysis:

Calculated for $C_{14}H_7BF_7NO_4 \cdot \frac{1}{2}H_2O$: C, 41.42% H; 1.99%; N, 3.45%. Found: C, 41.26%; H, 1.69%; N, 3.57%.

PREPARATION 11

5-Amino-1-cyclopropyl-8-difluoromethoxy-6,7-difluoro-1, 4-dihydro- 4-oxoquinoline 3-carboxylic acid [(XXII), $R^1$=—$OCHF_2$, $R^{17}$=H, X=F]

11(a) Diethyl (3-difluoromethoxy-2,4,5-trifluoro- 6-nitrobenzoyl )malonate [(XIV), $R^1$=—$OCHF_2$, $R^{3'}$=$NO_2$, $R^{17}$=$C_2H_5$, X=X'=F]

40 ml of thionyl chloride were added to a solution of 15.97 g (0.056 moles) of 3-difluoromethoxy-2,4,5-trifluoro-6-nitrobenzoic acid [(XII), $R^1$=—$OCHF_2$, $R^{3'}$=$NO_2$, X=X'= F] in 50 ml of benzene, and the mixture was heated under reflux for 2 hours. At the end of this time, the benzene and the excess thionyl chloride were removed by distillation under reduced pressure to give 16.50 g of 3-difluoromethoxy-2,4,5-trifluoro- 6-nitrobenzoyl chloride [(XIII), $R^1$=—$OCHF_2$, $R^{3'}$=$NO_2$, X=X'=F].

Meanwhile, a suspension of diethyl ethoxymagnesium malonate in diethyl ether was prepared from a mixture of 6.82 g (0.058 moles) of magnesium ethoxide and 9.35 g (0.058 moles) of diethyl malonate in 150 ml of anhydrous diethyl ether by heating under reflux for 2 hours, whilst stirring.

The whole of the 3-difluoromethoxy-2,4,5-trifluoro-6-nitrobenzoyl chloride [(XIII), $R^1$=—$OCHF_2$, $R^{3'}$=$NO_2$, X=X'=F] prepared as described above was dissolved in 150 ml of anhydrous diethyl ether, and this solution was added dropwise, with stirring at room temperature, to the suspension of diethyl ethoxymagnesium malonate. The resulting mixture was then stirred at room temperature for an additional 2 hours. At the end of this time, 100 ml of 1N aqueous hydrochloric acid were added to the reaction mixture, and, after the mixture had been vigorously stirred, the organic layer was separated, washed with water and dried over anhydrous sodium sulfate. The solvent was then removed by evaporation under reduced pressure to give 31.2 g of diethyl (3-difluoromethoxy-2,4,5-trifluoro-6-nitrobenzoyl)malonate [(XIV), $R^1$=—$OCHF_2$, $R^3$=$NO_2$, $R^{17}$=$C_2H_5$, X=X'=F] as a red liquid.

Mass Spectrum (CI): m/e 430 ($M^+$+1), 384 ($M^+$—OEt), 270 [$M^+$—$CH(COOEt)_2$].

11(b) Ethyl 3-difluoromethoxy-2,4,5-trifluoro-6-nitrobenzoylacetate [(XV), $R^1$=—$OCHF_2$, $R^3$=$NO_2$, $R^{17}$=$C_2H_5$, X=X'=F]

The whole of the diethyl (3-difluoromethoxy-2,4,5-trifluoro- 6-nitrobenzoyl)malonate [(XIV), $R^1$=—$OCHF_2$, $R^3$=$NO_2$, $R^{17}$=$C_2H_5$, X=X'=F] obtained as described in step (a) above was dissolved in 300 ml of dioxane, and 10.6 g (0.056 moles) of p-toluenesulfonic acid monohydrate were added to the resulting solution. The mixture was then heated under reflux for 4 hours. At the end of this time, the reaction mixture was concentrated by evaporation under reduced pressure. 150 ml of water and 4.7 g (0.056 moles) of sodium bicarbonate were added to the residue, which was then extracted with toluene. The extract was washed With water and dried over anhydrous sodium sulfate; the solvent was then removed by distillation under reduced pressure, to give 19.4 g of ethyl 3-difluoromethoxy-2,4,5-trifluoro-6-nitrobenzoylacetate as a red liquid.

Mass Spectrum (CI): m/e 358 ($M^+$+1), 312 ($M^+$—OEt), 270 ($M^+$—$CH_2CO_2Et$).

11(c) Ethyl 2-(3-difluoromethoxy-2,4,5-trifluoro- 6-nitrobenzoyl)-3-ethoxyacrylate [(XVI), $R^1$=—$OCHF_2$, $R^3$=$NO_2$, $R^{17}$=$C_2H_5$ X=X'=F]

38 ml of acetic anhydride and 11 ml of ethyl orthoformate were added to the whole of the ethyl 3-difluoromethoxy-2,4,5-trifluoro-6-nitrobenzoylacetate [(XV), $R^1$=—$OCHF_2$, $R^3$=$NO_2$, $R^{17}$=$C_2H_5$, X=X'=F] prepared as described in step (b) above, and then the mixture was heated under reflux for 3 hours; the excess acetic anhydride and ethyl orthoformate were then removed by evaporation under reduced pressure, to give 20.6 g of ethyl 2-(3-difluoromethoxy-2,4,5-trifluoro-6-nitrobenzoyl)-3-ethoxyacrylate as a red liquid.

Mass Spectrum (CI): m/e 414 ($M^+$+1), 367 ($M^+$—$NO_2$).

11(d) Ethyl 3-cyclopropylamino-2-(3-difluoromethoxy-2,4,5-trifluoro-6-nitrobenzoyl)acrylate [(XIX), $R^1$=—$OCHF_2$, $R^3$=$NO_2$, $R^{17}$=$C_2H_5$ X=X'=F]

The whole of the ethyl 2-(3-difluoromethoxy-2,4,5-trifluoro- 6-nitrobenzoyl)-3-ethoxyacrylate [(XVI), $R^1$=—$OCHF_2$, $R^3$=$NO_2$, $R^{17}$=$C_2H_5$, X=X'=F] obtained as described in step (c) above was dissolved in 500 ml of methylene chloride, and 3.5 g (0.06 moles) of cyclopropylamine were added dropwise to the resulting solution, whilst stirring and ice-cooling. The mixture was then stirred for 1 hour, whilst ice-cooling, and then for an additional 1 hour at room temperature, after which the solvent was removed by evaporation under reduced pressure. The resulting residue was subjected to silica gel column chromatography using a 9:1 by volume mixture of toluene and ethyl acetate as the eluent, to give 19.8 g of ethyl 3-cyclopropylamino-2-(3-difluoromethoxy-2,4,5-trifluoro-6-nitrobenzoyl)acrylate as an yellow powder, melting at 105°–106° C.

Mass Spectrum (CI): m/e 425 ($M^+$+1), 379 ($M^+$—OEt).

11(e) Ethyl 1-cyclopropyl-8-difluoromethoxy-6,7-difluoro-5-nitro-1,4-dihydro-4-oxoquinoline-3-carboxylate [(XX), $R^1$=—$OCHF_2$, $R^3$=$NO_2$, $R^{17}$=$C_2H_5$, X=F]

1.0 g (0.0024 moles) of ethyl 3-cyclopropylamino-2-(3-difluoromethoxy-2,4,5-trifluoro-8-nitrobenzoyl)acrylate [(XIX), $R^1$=—$OCHF_2$, $R^3$=$NO_2$, $R^{17}$=$C_2H_5$, X=X'=F] [prepared as described in step (d) above] was dissolved in 10 ml of tetrahydrofuran, and 0.094 g (0.0024 moles) of a 60% w/w suspension of sodium hydride in mineral oil was added to the resulting mixture. The mixture was then stirred at room temperature for 1 hour, after which 1N aqueous hydrochloric acid was added, and the mixture was vigorously stirred to acidify the whole mixture. The crystals which precipitated were collected by filtration and washed with water and with diethyl ether, in that order, to give 0.6 g of ethyl 1-cyclopropyl-8-difluoromethoxy- 6,7-difluoro-5-nitro-1,4-dihydro-4-oxo-quinoline-3-carboxylate as a pale yellow powder, melting at 262°–268° C.

Mass Spectrum (CI): m/e 405 ($M^+$+1), 358 ($M^+$—$NO_2$).

Nuclear Magnetic Resonance Spectrum (hexadeuterated dimethyl sulfoxide, δ ppm): 1.05 (4H, multiplier); 1.22 (3H, triplet); 3.91 (1H, multiplier); 4.18 (2H, quartet); 7.24 (1H, triplet, J=72 Hz) 8.56 (1H, singlet).

11(f) Ethyl 5-amino-1-cyclopropyl-8-difluoromethoxy-6,7-difluoro-1,4-dihydro-4-oxoquinoline-3-carboxylate [(XXII), $R^1$=—$OCHF_2$, $R^{17}$=$C_2H_5$, X=F]

3.0 g (0.0074 moles) of ethyl 1-cyclopropyl-8-difluoromethoxy- 6,7-difluoro-5-nitro-1,4-dihydro-4-oxoquinoline- 3-carboxylate [(XX), $R^1$=—$OCHF_2$, $R^3$=$NO_2$, $R^{17}$=$C_2H_5$, X=F] [prepared as described in step (e) above] were dissolved in 800 ml of acetic acid by heating. 0.75 g of 5% w/w palladium-on-carbon was then added to the solution, and the mixture was stirred at 70°–80° C. for 3 hours under a current of hydrogen. At the end of this time, the reaction mixture was filtered, and the filtrate was concentrated by evaporation under reduced pressure. The residue was washed with diethyl ether to give 1.78 g of ethyl 5-amino-1-cyclopropyl-8-difluoromethoxy-6,7-difluoro-1,4-dihydro-4-oxoquinoline-3-carboxylate as a colorless powder, melting at 295°–296° C.

Mass Spectrum (CI): m/e 375 ($M^+$+1), 329 ($M^+$—OEt).

11(f') Ethyl 5-amino-1-cyclopropyl-8-difluoromethoxy-6,7-difluoro-1,4-dihydro-4-oxoquinoline-3-carboxylate [(XXII), $R^1$=—$OCHF_2$, $R^{17}$=$C_2H_5$, X=F]

The compound of Preparation 11(f) was also synthesised by the following method.

33.63 g (0.079 mole) of ethyl 3-cyclopropylamino-2-(3-difluoromethoxy-2,4,5-trifluoro-6-nitrobenzoyl)acrylate [(XIXa): X=X'=F, $R^1$=$OCHF_2$, $R^{17}$=$C_2H_5$] were dissolved in 1300 ml of ethanol with heating. A stream of hydrogen was then bubbled through the solution in the presence of 8.4 g of 5% palladium-on-carbon at room temperature for 40 minutes, whilst stirring. At the end of this time, the reaction mixture was filtered, and the filtrate was concentrated by evaporation under reduced pressure. The resulting residue was then purified by silica gel column chromatography using a 9:1 by volume mixture of toluene and ethyl acetate as the eluent, to give 25.1 g of ethyl 3-cyclopropylamino-2-(6-amino-3-difluoromethoxy- 2,4,5-trifluorobenzoyl)acrylate [(XIXb): X=X' =F, $R^1$=$OCHF_2$, $R^{17}$=$C_2H_5$] as a pale yellow powder, melting at 103°–104° C.

Mass Spectrum (CI): m/e 395 ($M^+$+1).

The whole of the ethyl 3-cyclopropylamino-2-(6-amino-3-difluoromethoxy-2,4,5-trifluorobenzoyl)acrylate prepared as described above was dissolved in 340 ml of tetrahydrofuran, and 3.82 g (0.096 mole) of a 60% w/w dispersion of sodium hydride in mineral oil were added slowly to the resulting solution, whilst ice-cooling. The mixture was then stirred at the same temperature for 30 minutes, and then at room temperature for a further 1 hour. At the end of this time, the reaction mixture was acidified by the addition of 96 ml of 1N aqueous hydrochloric acid, whilst stirring vigorously. The resulting precipitate was collected by filtration and washed with water and with ethanol, in that order, to give 18.76 g of ethyl 5-amino-1-cyclopropyl-8-difluoromethoxy- 6,7-difluoro-1,4-dihydro-4-oxoquinoline-3-carboxylate [(XXII), $R^1$=—$OCHF_2$, $R^{17}$=$C_2H_5$, X=F] as a colorless powder, melting at 295°–296° C.

Mass Spectrum (CI): m/e 375 ($M^+$+1).

11(g) 5-Amino-1-cyclopropyl-8-difluoromethoxy-6,7-difluoro- 1,4-dihydro-4-oxoquinoline-3-carboxylic acid [(XXI) $R^1$=—$OCHF_2$, $R^3$=$NH_2$, X=F]

A suspension of 3.58 g (0.0096 moles) of ethyl 5-amino-1-cyclopropyl-8-difluoromethoxy-6,7-difluoro-1,4-dihydro-4-oxoquinoline-3-carboxylate [(XXII), $R^1$=—$OCHF_2$, $R^{17}$=$C_2H_5$, X=F] [prepared as described in step (f) or (f') above], 21 ml of acetic acid, 2.8 ml of concentrated sulfuric acid and 15 ml of water was heated under reflux, with stirring, for 1 hour, after which it was cooled by allowing it to stand. Water was then added to the reaction mixture, and the insoluble materials were removed by filtration and washed with water and with diethyl ether, in that order, to give 3.0 g of 5-amino-1-cyclopropyl-8-difluoromethoxy- 6,7-difluoro-1, 4-dihydro-4-oxoquinoline-3-carboxylic acid as a pale yellowish green powder, melting at 284°–286° C.

Mass Spectrum (CI): m/e 347 ($M^+$+1), 329 ($M^+$—OH), 302 ($M^+$—$CO_2$).

Nuclear Magnetic Resonance Spectrum (hexadeuterated dimethyl sulfoxide, δ ppm): 0.8–1.2 (4H, multiplier); 3.92 (1H, multiplier); 7.05 (1H, triplet, J=73 Hz); 7.92 (2H, broad singlet); 8.62 (1H, singlet); 14.25 (1H, singlet).

Elemental analysis: Calculated for $C_{14}H_{10}F_4N_2O_4$: C, 48.57%; H, 2.91%; N, 8.09%. Found: C, 48.45%; H, 2.53%; N, 8.03%.

PREPARATION 12

5-Amino-1-cyclopropyl-8-difluoromethoxy-6,7-difluoro-1, 4-dihydro-4-oxoquinoline-3-carboxylic acid boron difluoride chelate [(IX), $R^1$=—$OCHF_2$, $R^3$=$NH_2$, X=F]

0.96 g of boron trifluoride.diethyl etherate was added to a mixture of 1.17 g (0.0034 mole) of 5-amino-1-cyclopropyl-8-difluoromethoxy-6,7-difluoro-1,4-dihydro-4-oxoquinoline-3-carboxylic acid [(XXI), $R^1$=—$OCHF_2$, $R^3$=$NH_2$, X=F, or (VI), $R^1$=—$OCHF_2$, $R^3$=$NH_2$, $R^{13}$=H, X=F] (prepared as described in Preparation 11) and 30 ml of methyl isobutyl ketone, and the mixture was heated under reflux for 6 hours. At the end of this time, the mixture was cooled with ice, and the crystals which precipitated from the reaction mixture were collected by filtration and washed with diethyl ether to afford 1.29 g of 5-amino-1-cyclopropyl-8-difluoromethoxy-6,7-difluoro-1,4-dihydro-4-oxoquinoline- 3-carboxylic acid boron difluoride chelate as yellow crystals, melting at not less than 300° C.

Mass Spectrum (CI): m/e 395 ($M^+$+1).

Elemental analysis: Calculated for $C_{14}H_9BF_6N_2O_4$: C, 42.68%; H. 2.30%; N. 7.11%. Found: C, 42.29%; H. 2.30%; N. 7.08%.

PREPARATION 13

2,4,5-Trifluoro-3-hydroxybenzoic acid [(XXIII), X=X'=F]
2700 g of 3,5,6-trifluoro-4-hydroxyphthalic acid and 6 liters of water were placed in an autoclave, and the mixture was heated at 140° C for 3 hours in an atmosphere of nitrogen. At the end of this time, the reaction mixture was cooled to room temperature and concentrated by evaporation under reduced pressure, to precipitate crystals, which were collected by filtration, washed with chloroform and dried to give 1623 g of 2,4,5-trifluoro- 3-hydroxybenzoic acid [(XXIII), X =X'=F] as a colorless powder, melting at 144°–146° C.

Mass Spectrum: m/e 192 ($M^+$).

Nuclear Magnetic Resonance Spectrum ($CD_3OD$, δ ppm): 4.94 (1H, broad singlet); 7.25 (1H, multiplier).

PREPARATION 14

(2S)-Methylpiperazine

14(a) Ethyl N-cyanomethyl-L-alanate 10 ml of water, followed by 3.2 g (0.065 mole) of Sodium cyanide, were added to 10 g (0.065 mole) of ethyl L-alanate hydrochloride. 5.3 g (0.065 mole) of a solution of 37% by weight of formaldehyde in water were then added dropwise to the mixture. During this addition, the reaction temperature increased to nearly 40° C. The resulting mixture was then stirred at room temperature for 6 hours, after which it was allowed to stand overnight at the same temperature. The reaction mixture was then extracted with methylene chloride, and the organic extract was washed with a saturated aqueous solution of sodium bicarbonate and with water, in that order. It was then dried over anhydrous sodium sulfate and concentrated by evaporation under reduced pressure. The residue was purified by column chromatography through silica gel, using a 9:1 by volume mixture of toluene and ethyl acetate as the eluent, to afford 5.6 g of ethyl N-cyanomethyl-L-alanate as a colorless oil.

Mass Spectrum (CI): m/e 157 ($M^+$+1), 130 ($M^+$—CN).

Nuclear Magnetic Resonance Spectrum ($CDCl_3$) δ ppm: 1.28 (3H, triplet, J=6 Hz); 1.33 (3H, doublet, J=6 Hz); 2.15 (1H, singlet); 3.45 (1H, quartet, J=6 Hz); 3.60 (2H, singlet; 4.20 (2H, quartet, J=6 Hz).

14(b) (3S)-Methyl-2-oxopiperazine

A mixture of 5.0 g (0.321 mole) of ethyl N-cyano-methyl-L-alanate [prepared as described in step (a) above], 56 g of ethanol containing 4% w/w ammonia and 1.38 g of Raney nickel was transferred to an autoclave where it was then stirred under a hydrogen pressure of 50 kg/cm$^2$ at 90° C. for 2 hours. At the end of this time, the catalyst was removed by filtration and the solvent was stripped from the filtrate by evaporation under reduced pressure. The residue was purified by column chromatography through silica gel using a 1:20 by volume mixture of methanol and chloroform as the eluent, to afford 2.8 g of (3S)-methyl-2-oxopiperazine as colorless crystals.

Mass Spectrum (CI): m/e 115 ($M^+$+1).

Nuclear Magnetic Resonance Spectrum ($CDCl_3$) δ ppm: 1.40 (3H, doublet, J=6 Hz); 1.78 (1H, singlet); 2.9–3.6 (5H, multiplet); 7.00 (1H, broad).

14(c) (2S)-Methyl piperazine

A solution of 2.29 g (0.020 mole) of (3S)-methyl-2-oxopiperazine [prepared as described in step (b) above] in 35 ml of tetrahydrofuran was added dropwise to a suspension of 1.53 g (0.040 mole) of lithium aluminum hydride in 35 ml of tetrahydrofuran, and the mixture was heated under reflux for 5 hours. It was then allowed to cool, after which a small amount of water was added to the reaction mixture, whilst ice-cooling, to decompose any excess of the reducing agent. The reaction mixture was then filtered, and the filtrate was mixed with 10 ml of concentrated aqueous hydrochloric acid and evaporated to dryness under reduced pressure. The residue was triturated with a mixture of diethyl ether and ethanol to give 2.73 g of (2S)-methylpiperazine dihydrochloride as a colorless powder, which was dissolved in 10 ml of water. The pH of the aqueous solution was adjusted to a value greater than 10 by the addition of a 10% w/v aqueous solution of sodium hydroxide, and then the mixture was extracted with chloroform. The chloroform extract was dried over anhydrous sodium sulfate and the solvent was removed by evaporation under reduced pressure. 1.30 g of (2S)-methylpiperazine was obtained as colorless needles by vacuum distillation of the residue. It was determined by high pressure liquid chromatography analysis [using GITC (2,3,4,6-tetra-O-acetyl-β-D-glucopyranosyl isothiocyanate) derivatives] that the product was an S-isomer having an optical purity of 98.5%.

Mass Spectrum (CI): m/e 101 ($M^+$+1).

Nuclear Magnetic Resonance Spectrum ($CDCl_3$) δ ppm: 1.00 (3H, doublet, J=6 Hz); 1.85 (2H, singlet); 2.30–2.45 (1H, multiplier); 2.6–3.0 (6H, multiplier).

PREPARATIONS 15–18

Following a procedure similar to that described in Preparation 14, but using the starting materials listed in Table 2, the following piperazine derivatives were synthesized.

TABLE 2

| Preparation No. | Starting material | Product (piperazines) | m.p.(°C.) |
|---|---|---|---|
| 15 | L-α-aminobutyric acid | (2S)-ethyl-piperazine 2HCl | 231–234 |
| 16 | L-valine | (2S)-isopropyl-piperazine 2HCl | 261–264 |
| 17 | 2-aminoisobutyric acid | 2,2-dimethyl-piperazine 2HCl | 229–240 |
| 18 | DL-O-methylserine | DL-2-methoxymethylpiperazine 2HCl | 199–204 |

PREPARATION 19

(3S)-Aminopyrrolidine dihydrochloride

19(a) Ethyl N-t-butoxycarbonyl-L-aspartate 7.33 g (0.072 mole) of triethylamine were added, whilst ice-cooling, to a solution of 14.88 g (0.066 mole) of ethyl L-aspartate hydrochloride dissolved in 200 ml of methylene chloride. The mixture was then stirred for 20 minutes, after which 14.4 g (0.066 mole) of di-t-butyl dicarbonate were added to it in portions. When the addition was complete, the mixture was stirred for 2 hours and then concentrated by evaporation under reduced pressure. Toluene was added to the residue, and the triethylamine hydrochloride which precipitated was removed by filtration. The filtrate was concentrated by evaporation under reduced pressure, and the residue was purified by column chromatography through silica gel, using a 4:1 by volume mixture of toluene and ethyl acetate as the eluent, to afford 18.61 g of ethyl N-t-butoxycarbonyl-L-aspartate as a colorless oil.

Mass Spectrum (CI): m/e 234 ($M^+$+1—$CH_2$=$C(CH_3)_2$), 190 ($M^+$+1—$CO_2$—$CH_2$=$C(CH_3)_2$).

19(b) (2S)-t-Butoxycarbonylamino-1,4-dihydroxybutane 40 ml of tetrahydrofuran containing 10.0 g (0.035 mole) of ethyl N-t-butoxycarbonyl-L-aspartate [prepared as described in step (a) above] were added dropwise to a solution of 3.01 g (0.138 mole) of lithium borohydride dissolved in 100 ml of tetrahydrofuran. The dropping rate was adjusted so that the reaction temperature was maintained at 40° C. After completion of the addition, the mixture was stirred at room temperature for 4 hours. At the end of this time, any excess of the reducing agent was decomposed by the addition of a small amount of water. The reaction mixture was then filtered, and the filtrate was concentrated by evaporation under reduced pressure, to remove the tetrahydrofuran. Sodium chloride was then added, and the mixture was extracted with ethyl acetate. The organic extract was dried over anhydrous sodium sulfate and concentrated by evaporation under reduced pressure, to afford 6.15 g of (2S)-t-butoxycarbonylamino- 1,4-dihydroxybutane as a colorless oil.

Mass Spectrum (CI): m/e 206 ($M^+$+1 ), 150 ($M^+$+1—$CH_2$=$C(CH_3)_2$), 106 ($M^+$+1 —$CO_2$—$CH_2$=$C(CH_3)_2$).

19(c) (2S)-t-Butoxycarbonylamino-1,4-di(methylsulfonyloxy)butane 15.12 g (0.132 mole) of methanesulfonyl chloride were added dropwise, whilst ice-cooling, to a solution of 13.0 g (0.060 mole) of (2S)-t-butoxycarbonylamino-1,4-dihydroxybutane [prepared as described in step (b) above] and 14.54 g (0.144 mole) of triethylamine in 250 ml of methylene chloride. The mixture was stirred for 3 hours, whilst ice-cooling, after which it was allowed to stand overnight at room temperature. At the end of this time, it was mixed with water and with methylene chloride. The organic layer was separated and dried over anhydrous sodium sulfate, and then the dried organic layer was concentrated by evaporation under reduced pressure, to give 20.22 g of (2S)-t-butoxycarbonylamino- 1,4-di(methylsulfonyloxy)butane as colorless crystals.

Mass Spectrum (CI): m/e 210 ($M^+$—$OSO_2CH_3$—$CH_2$=$C(CH_3)_2$).

19 (d) (3S)-Aminopyrrolidine dihydrochloride 6.0 g (0.059 mole) of triethylamine were added to a suspension of 20.22 g (0.056 mole) of (2S)-t-butoxycarbonylamino- 1,4-di(methylsulfonyloxy)butane [prepared as described in step (c) above] in 130 ml of methanol. Ammonia gas was passed into the mixture until it reached saturation, and the mixture was then stirred at room temperature for 2 days. At the end of this time, it was concentrated by evaporation under reduced pressure. The resulting residue was dissolved in 150 ml of methylene chloride, and then 12.22 g (0.056 mole) of di-t-butyl dicarbonate were added to the resulting solution. 23 ml of triethylamine were then added dropwise, and the mixture was stirred at room temperature for 2 hours. The reaction mixture was then washed with water and dried over anhydrous sodium sulfate, after which it was concentrated by evaporation under reduced pressure. The residue was purified by column chromatography through silica gel using a 9:1 by volume mixture of toluene and ethyl acetate as the eluent, to afford (3S)-t-butoxycarbonylamino-1-t-butoxycarbonylpyrrolidine as a colorless oil. The oil was mixed with 10 ml of concentrated aqueous hydrochloric acid, and the mixture was evaporated to dryness under reduced pressure, and triturated with ethanol to give 2.87 g of (3S)-aminopyrrolidine dihydrochloride as a colorless powder.

Mass Spectrum (CI): m/e 87 ($M^+$+1), 70 ($M^+$—$NH_2$).

PREPARATION 20

3-Amino-4-(2,2,2-trifluoroethoxy)pyrrolidine dihydrochloride

20(a) 1-t-Butoxycarbonyl-3-(2,2,2-trifluoroethoxy) 4-methylsulfonyloxypyrrolidine 1.08 g (0.027 mole) of a §0% w/w dispersion of sodium hydride in mineral oil was added, whilst cooling with water, to 15 ml of 2,2,2-trifluoroethanol, and the mixture was stirred for 20 minutes. At the end of this time, 5.0 g (0.027 mole) of 1-t-butoxycarbonyl-3,4-epoxypyrrolidine were added to the mixture, which was then heated under reflux for 3 hours. The reaction mixture was then mixed with a saturated aqueous solution of sodium chloride and extracted with ethyl acetate. The organic extract was dried over anhydrous sodium sulfate and concentrated by evaporation under reduced pressure. The concentrate was dissolved in 50 ml of pyridine, and 3.23 g (0.028 mole) of methanesulfonyl chloride were added, whilst ice-cooling, to the resulting solution. The mixture was then stirred at room temperature for 5 hours and then allowed to stand overnight at room temperature. After it had been diluted with 300 ml of water, the reaction mixture was extracted with toluene. The organic extract was dried over anhydrous sodium sulfate and concentrated by evaporation under reduced pressure. The residue was purified by column chromatography through silica gel using a 9:1 by volume mixture of toluene and ethyl acetate as the eluent, to afford 7.07 g of 1-t-butoxycarbonyl-1-3-(2,2,2-trifluoroethoxy)-4-methylsulfonyloxy-pyrrolidine.

20(b) 3-Amino-1-t-butoxycarbonyl-4-(2,2,2-trifluoroethoxy)pyrrolidine

A mixture of 3.95 g (0.011 mole) of 1-t-butoxycarbonyl-3-(2,2,2-trifluoroethoxy)-4-methylsulfonyloxypyrrolidine [prepared as described in step (a) above] and 100 ml of methanol containing 20% w/v ammonia was transferred to an autoclave and then stirred at 140° C. for 10 hours. At the end of this time, the solvent was removed by distillation under reduced pressure, and the residue was mixed with a saturated aqueous solution of sodium carbonate and extracted with ethyl acetate. The organic extract was dried over anhydrous sodium sulfate and concentrated by evaporation under reduced pressure. The residue was purified by column chromatography through silica gel using a 1:9 by volume mixture of ethanol and ethyl acetate as the eluent to give 1.61 g of 3-amino-1-t-butoxycarbonyl-4-(2,2,2-trifluoroethoxy)pyrrolidine as a colorless oil.

Mass Spectrum (CI)- m/e 285 ($M^+$+1). 229 ($M^+$1—$CH_2$=$C(CH_3)_2$ ).

20(c) 3-Amino-4-(2,2,2-trifluoroethoxy)pyrrolidine dihydrochloride

A mixture of 1.61 g (0.006 mole) of 3-amino-1-t-butoxycarbonyl-1-4-(2,2,2-trifluoroethoxy)pyrrolidine [prepared as described in step (b) above], 30 ml of ethanol, 2 ml of concentrated aqueous hydrochloric acid and 4 ml of water was allowed to stand overnight an room temperature after which in was evaporated to dryness under reduced pressure, to afford 1.60 g of 3-amino-4-(2,2,2-trifluoroethoxy)pyrrolidine dihydrochloride as colorless crystals.

Mass Spectrum (CI): m/e 185 ($M^+$+1).

PREPARATION 21

3-Amino-4-methoxymethylpyrrolidine dihydrochloride

21(a) 1-Benzyl-3-ethoxycarbonyl-4-hydroxyiminopyrrolidine

A solution of 24.7 g (0.1 mole) of 1-benzyl-3-ethoxycarbonyl-4-pyrrolidone in 135 ml of ethanol was added dropwise at room temperature to a solution of 34.7 g (0.5 mole) of hydroxylamine hydrochloride dissolved in 135 ml of water, and then 28.1 g (0.265 mole) of sodium carbonate were added to the mixture. The mixture was then stirred at room temperature for 6.5 hours, after which it was extracted with 300 ml of chloroform. The chloroform extract was washed with water and dried over anhydrous sodium sulfate. It was then concentrated by evaporation under reduced pressure. The residue was purified by column chromatography through silica gel using a 2:1 by volume mixture of toluene and ethyl acetate as the eluent, to afford 15.8 g of 1-benzyl-3-ethoxycarbonyl-4-hydroxyiminopyrrolidine as a brown oil.

Mass Spectrum (CI): m/e 263 ($M^+$+1).

Infrared Absorption Spectrum (capillary) $v_{max}$ $cm^{-1}$: 3300, 1740.

21(b) 3-Amino-1-benzyl-4-hydroxymethylpyrrolidine

A solution of 5.24 g (0.02 mole) of 1-benzyl-3-ethoxycarbonyl- 4-hydroxyiminopyrrolidine [prepared as described in step (a) above] in 10 ml of toluene was added dropwise to 28 ml of a 3.4M solution of sodium bis(2-methoxyethoxy)aluminum hydride in toluene over a period of 1 hour. The mixture was stirred at room temperature for 1.5 hours and was then heated under reflux for 2 hours. At the end of this time, the reaction mixture was allowed to cool to room temperature, after which ice and water were added to it to form a precipitate, which was removed by filtration. The filtrate was concentrated by evaporation under reduced pressure, and the residue was purified by column chromatography through silica gel using methanol as the eluent, to afford 2.16 g of 3-amino-1-benzyl-4-hydroxymethylpyrrolidine as a brown oil.

Mass Spectrum (CI): m/e 207 ($M^+$+1).

Infrared Absorption Spectrum (capillary) $v_{max}$ $cm^{-1}$: 3150–3400.

21(c) 1-Benzyl-3-(N-t-butoxycarbonyl)amino-4-hydroxylmethylpyrrolidine 6.21 g (0.0285 mole) of di-t-butyl dicarbonate were added in portions at room temperature to a solution of 5.87 g (0.0285 mole) of 3-amino-1-benzyl-4-hydroxymethylpyrrolidine [prepared as described in step (b) above] in 100 ml of methylene chloride. The mixture was stirred at room temperature for 1 day and then the solvent was removed by distillation under reduced pressure. The residue was purified by column chromatography through silica gel using ethyl acetate as the eluent, to afford 6.32 g of 1-benzyl-3-(N-t-butoxycarbonyl)amino-4-hydroxymethylpyrrolidine as a pale brown oil.

Infrared Absorption Spectrum (capillary) $v_{max}$ $cm^{-1}$: 3350, 1680–1720.

21(d) 3-(N-t-Butoxycarbonyl)amino-4-hydroxymethylpyrrolidine

A mixture of a solution of 6.32 g (0.0207 mole) of 1-benzyl-3-(N-t-butoxycarbonyl)amino-4-hydroxymethylpyrrolidine [prepared as described in step (c) above] dissolved in 100 ml of ethanol and 2.0 g of 20% w/w palladium-on-carbon was transferred to a stainless steel autoclave and stirred at room temperature under a hydrogen pressure of 100 kg/$cm^2$ for 27 hours. At the end of this time, the catalyst was removed by filtration, and the filtrate was concentrated by evaporation under reduced pressure, to afford 3.99 g of 3-(N-t-butoxycarbonyl)amino-4-hydroxymethylpyrrolidine as a colorless crystalline oil.

Mass Spectrum (CI): m/e 217 ($M^+$+1).

Infrared Absorption Spectrum (KBr) $v_{max}$ $cm^{-1}$: 3350, 3270, 1680–1690.

21(e) 1-t-Butoxycarbonyl-3-(N-t-butoxycarbonyl)amino-4-hydroxymethylpyrrolidine 3.12 g of di-t-butyl dicarbonate were added in portions at room temperature to a solution of 3.08 g (0.0143 mole) of 3-(N-t-butoxycarbonyl)amino-4-hydroxymethylpyrrolidine [prepared as described in step (d) above] in 50 ml of methylene chloride, and the mixture was stirred at room temperature for one day. At the end of this time, the solvent was distilled off under reduced pressure. The residue was purified by column chromatography through silica gel using a 1:1 by volume mixture of toluene and ethyl acetate as the eluent, to afford 3.99 g of 1-t-butoxycarbonyl-3-(N-t-butoxycarbonyl)amino- 4-hydroxymethylpyrrolidine as colorless crystals.

Mass Spectrum (CI): m/e 317 ($M^+$+1).
21(f) 1-t-Butoxycarbonyl-3-(N-t-butoxycarbonyl)amino-4-methoxymethylpyrrolidine 0.3 ml of boron trifluoride.diethyl etherate was added dropwise to a solution of 3.86 g (0.0122 mole) of 1-t-butoxycarbonyl-3-(N-t-butoxycarbonyl ) amino-4-hydroxymethylpyrrolidine [prepared as described in step (e) above] in 190 ml of diethyl ether cooled with ice, and then an ethereal solution containing 0.126 mole of diazomethane was added to the mixture over a period of 1.5 hours. The mixture was stirred at the same temperature for 0.5 hour, after which it was allowed to stand overnight at room temperature. It was then mixed with a saturated aqueous solution of sodium chloride and the ethereal layer was separated. The ethereal layer was dried, and then the solvent was distilled off under reduced pressure. The residue was purified by column chromatography through silica gel using a 2:1 by volume mixture of toluene and ethyl acetate as the eluent to afford 0.47 g of 1-t-butoxycarbonyl-3-(N-t-butoxycarbonyl)amino- 4-methoxymethylpyrrolidine as a colorless oil.

Mass Spectrum (CI): m/e 331 ($M^+$+1).
Infrared Absorption Spectrum (capillary) $v_{max}$ cm$^{-1}$: 3330, 1670–1730.
21(g) 3-Amino-4-methoxymethylpyrrolidine dihydrochloride 7 ml of 6N aqueous hydrochloric acid were added to a solution of 0.58 g (0.0021 mole) of 1-t-butoxycarbonyl-3-(N-t-butoxycarbonyl)amino-4-methoxymethylpyrrolidine [prepared as described in step (f) above] in 30 ml of ethanol. The mixture was then heated under reflux for 2 hours, after which it was evaporated to dryness under reduced pressure to give 0.43 g of 3-amino-4-methoxymethylpyrrolidine dihydrochloride as a brown oil.

Mass Spectrum (CI): m/e 131 ($M^+$+1).

PREPARATION 22

2-Fluoromethylpiperazine dihydrochloride

22(a) N-Benzyl-N-(3-fluoro-2-hydroxypropyl)ethanolamine

A solution of 22.20 g (0.3 mole) of epifluorohydrin and 67.95 g (0.45 mole) of N-benzylethanolamine dissolved in 200 ml of ethanol was heated under reflux for 5 hours. At the end of this time, the reaction mixture was concentrated by evaporation under reduced pressure, and the residue was purified by column chromatography through silica gel using ethyl acetate as the eluent, to give 64.93 g of N-benzyl-N-(3-fluoro-2-hydroxypropyl)ethanolamine as a colorless oil.

Mass Spectrum (CI): m/e 228 ($M^+$+1).
22(b) N-(3-Fluoro-2-methylsulfonyloxypropyl)-N-(2-methylsulfonyloxyethyl)benzylamine 7.27 g (0.072 mole) of triethylamine were added to a solution of 6.75 g (0.03 mole) of N-benzyl-N-(3-fluoro-2-hydroxypropyl)ethanolamine [prepared as described in step (a) above] in 200 ml of ethyl acetate. Whilst stirring and ice-cooling the mixture, 8.24 g (0.072 mole) of methanesulfonyl chloride were added to it. After the resulting mixture had been stirred for 3 hours at the same temperature, an aqueous solution of sodium bicarbonate was added to it. The organic layer was separated, washed with water and dried over anhydrous sodium sulfate. The solvent was then removed by distillation under reduced pressure, to give 12.49 g of N-(3-fluoro-2-methylsulfonyloxypropyl)-N-(2-methylsulfonyloxyethyl)benzylamine as a pale yellow oil.

Mass Spectrum (CI): m/e 384 ($M^+$+1).
22(c) 1,4-Dibenzyl-2-fluoromethylpiperazine 4.82 g (0.045 mole) of benzylamine and 9.09 g (0.09 mole) of triethylamine were added to a solution of N-(3-fluoro-2-methylsulfonyloxypropyl)-N-(2-methylsulfonyloxyethyl)benzylamine [prepared as described in step (b) above] dissolved in 200 ml of ethanol. The mixture was heated under reflux for 2 hours and then concentrated by evaporation under reduced pressure. 100 ml of ethanol and 40 ml of a 2N aqueous solution of sodium hydroxide were added to the residue, and the mixture was concentrated by evaporation under reduced pressure. The residue was mixed with ethyl acetate, and insoluble materials were removed by filtration. The filtrate was freed from the solvent by evaporation under reduced pressure, and the residue was purified by column chromatography through silica gel using a 9:1 by volume mixture of toluene and ethyl acetate as the eluent, to afford 3.60 g of 1,4-dibenzyl-2-fluoromethylpiperazine as a yellow oil.

Mass Spectrum (CI): 299 ($M^+$+1).
22(d) 2-Fluoromethylpiperazine dihydrochloride A mixture of a solution of 23.85 g (0.08 mole) of 1,4-dibenzyl-2-fluoromethyl piperazine [prepared as described in step (c) above] in 500 ml of methanol and 33 ml of concentrated aqueous, hydrochloric acid was stirred vigorously at room temperature for 1 hour in an atmosphere of hydrogen and in the presence of 1.0 g of 20% w/w palladium-on-carbon. At the end of this time, the catalyst was removed by filtration and washed with water. The filtrate and washings were concentrated by evaporation under reduced pressure, and the residue was dissolved in 200 ml of water. The resulting aqueous solution was washed vigorously with ethyl acetate and separated. The aqueous layer was concentrated by evaporation under reduced pressure, and the residue was washed with ethanol to afford 13.76 g of 2-fluoromethylpiperazine dihydrochloride as a colorless powder, melting at 205°–218° C.

Mass Spectrum (CI): m/e 119 ($M^+$+1).
Elemental analysis: Calculated for $C_5H_{13}Cl_2FN_2$: C, 31.43%; H, 6.86%; N, 14.66%. Found: C, 31.42%; H, 6.81%; N, 14.71%.

PREPARATION 23

(2S)-Methylhomopiperazine dihydrochloride

23(a) Ethyl N-cyanoethyl-L-alanate

A solution of 15.3 g (0.131 mole) of ethyl L-alanate, 7.0 g (0.132 mole) of acrylonitrile and 1.0 g (0.018 mole) of sodium methoxide dissolved in 150 ml of ethanol was heated under reflux for 7 hours. After it had been allowed to cool, the reaction mixture was concentrated by evaporation under reduced pressure, and the residue was purified by column chromatography through silica gel using a 4:1 by volume mixture of toluene and ethyl acetate as the eluent, to afford 12.5 g of ethyl N-cyanoethyl-L-alanate as a colorless oil.

Mass Spectrum (CI): m/e 171 ($M^+$+1).

23(b) (3S)-Methyl-2-oxohomopiperazine

A mixture of 9.8 g (0.057 mole) of ethyl N-cyanoethyl-L-alanate [prepared as described in step (a) above], 70 g of ethanol containing 4% w/w ammonia and 1.79 g of Raney nickel was transferred to an autoclave and then stirred under a hydrogen pressure of 60 kg/cm$^2$ at 90° C. for 3 hours. After the mixture had been allowed to cool, the catalyst was removed by filtration and the filtrate was concentrated by evaporation under reduced pressure. The residue was mixed with 200 ml of xylene and 1.4 g of dibutyltin oxide, and the mixture was heated under reflux for 10 hours. A fraction containing ethanol, formed during the reaction, was eliminated from the reaction system. Subsequently, the reaction mixture was concentrated by evaporation under reduced pressure, and the residue was purified by column chromatography through silica gel using a 9:1 by volume mixture of chloroform and methanol as the eluent, to afford 5.3 g of (3S)-methyl-2-oxohomopiperazine as pale brown crystals.

Mass Spectrum (CI): m/e 129 (M$^+$+1).

23(c) (2S)-Methylhomopiperazine dihydrochloride

A mixture of 4.92 g (0.038 mole) of (3S)-methyl-2-oxohomopiperazine [prepared as described in step (b) above] in 60 ml of tetrahydrofuran was added dropwise, whilst ice-cooling, to a suspension of 2.91 g (0.077 mole) of lithium aluminum hydride in 60 ml of tetrahydrofuran, and the mixture was heated under reflux for 5 hours. After the reaction mixture had been allowed to cool, a small amount of water was added to it, whilst ice-cooling, to decompose any excess of the reducing agent. The reaction mixture was then filtered, and 20 ml of concentrated aqueous hydrochloric acid were added to the filtrate, which was then evaporated to dryness under reduced pressure. The residue was triturated with ethanol, to give 5.93 g of (2S)-methylhomopiperazine dihydrochloride as colorless crystals, melting at 211°–220° C.

Mass Spectrum (CI): m/e 115 (M$^+$+1).

PREPARATION 24

2,6-Bis(fluoromethyl)piperazine dihydrochloride

24(a) N,N-Bis(3-fluoro-2-hydroxypropyl)benzylamine

A solution of 27.28 g (0.359 mole) of epifluorohydrin and 19.20 g (0.1795 mole) of benzylamine dissolved in 200 ml of ethanol was heated under reflux for 4 hours. The reaction mixture was then concentrated by evaporation under reduced pressure, to give 46.6 g of N,N-bis(3-fluoro-2-hydroxypropyl)benzylamine as a colorless oil.

Mass Spectrum (CI): m/e 260 (M$^+$+1).

24(b) 1,4-Dibenzyl-2,6-bis(fluoromethyl)piperazine 28.89 g (0.286 mole) of triethylamine were added to a solution of 33.67 g (0.13 mole) of N,N-bis(3-fluoro- 2-hydroxypropyl)benzylamine [prepared as described in step (a) above] in 300 ml of tetrahydrofuran. 32.76 g (0.286 mole) of methanesulfonyl chloride were then added dropwise to the mixture, whilst ice-cooling. After the mixture had been stirred at room temperature for 6 hours, 39.40 g (0.39 mole) of triethylamine, 20.87 g (0.195 mole) of benzylamine and 300 ml of ethanol were added to it, and it was then heated under reflux for 3 hours. At the end of this time, the reaction mixture was concentrated by evaporation under reduced pressure, and 300 ml of water containing 30 g of sodium hydroxide were added to the residue. The aqueous mixture thus obtained was extracted with ethyl acetate and the organic extracts were washed with water, dried over anhydrous sodium sulfate and concentrated by evaporation under reduced pressure. The residue was purified by column chromatography through silica gel using a 20:1 by volume mixture of toluene and ethyl acetate as the eluent, to afford 1,4-dibenzyl-2,6-bis(fluoromethyl)piperazine, including 6.29 g of isomer A and 6.60 g of isomer B, as colorless crystals.

Rf value of isomer A: 0.7

Rf value of isomer B: 0.5

(Thin layer plane: silica gel F$_{254}$. Merck; Developing solvent: a 9:1 by volume mixture of toluene and ethyl acetate)

Mass Spectrum (CI) of both isomers A and B: m/e 331 (M$^+$+1).

24(c) 2,6-Bis(fluoromethyl)piperazine dihydrochloride

A mixture of a suspension of 5.03 g (0.015 mole) of 1,4-dibenzyl-2,6-bis(fluoromethyl)piperazine isomer B [prepared as described in step (b) above] in 130 ml of methanol and 6 ml of concentrated aqueous hydrochloric acid was stirred vigorously under a stream of hydrogen at room temperature for 1 hour in the presence of 0.6 g of 20% w/w palladium-on-carbon. At the end of this time, the catalyst was removed by filtration, and the filtrate was concentrated by evaporation under reduced pressure. The residue was mixed with 50 ml of water, and the resulting insoluble materials were removed by filtration. The filtrate was concentrated by evaporation under reduced pressure, and the residue was washed with ethanol, to afford 3.10 g of 2,6-bis(fluoromethyl)piperazine (isomer B) dihydrochloride as a colorless powder, melting at 207°–225° C.

Mass Spectrum (CI): m/e 151 (M$^+$+1).

Elemental analysis: Calculated for $C_6H_{14}Cl_2F_2N_2$: C, 32.30%; H, 6.32%; N, 12.56%.

Found: C, 32.38%; H, 6.26%; N, 12.60%. The above procedure was repeated but using 1,4-dibenzyl-2,6-bis(fluoromethyl)piperazine (isomer A) to afford 2,6-bis(fluoromethyl)piperazine (isomer A) dihydrochloride as a colorless powder.

Mass Spectrum (CI): m/e 151 (M$^+$+1).

Elemental analysis: Calculated for $C_6H_{14}Cl_2F_2N_2 \cdot \frac{1}{2}H_2O$: C, 31.04%; H, 6.51%; N, 12.07%. Found: C, 30.66%; H, 6.22%; N, 11.78%.

EXAMPLE 1

1-Cyclopropyl-8-difluoromethoxy-6-fluoro-7-(3-methylpiperazinyl)- 1,4-dihydro-4-oxoquinoline-3-carboxylic acid 1.63 g (0.016 moles) of 2-methylpiperazine was added to a solution of 2.58 g (0.0068 mole) of 1-cyclopropyl-8-difluoromethoxy-6,7-difluoro-1,4-dihydro-4-oxoquinoline-3-carboxylic acid boron difluoride chelate (prepared as described in Preparation 8) in 20 ml of dimethyl sulfoxide, and the mixture was allowed to stand at room temperature overnight. The reaction mixture was then poured into 100 ml of water, and the crystals which precipitated were collected by filtration and washed with water. The crystals were then dissolved in 500 ml of 80% v/v aqueous methanol containing 15 ml of triethylamine, and the solution was heated under reflux for 3 hours. At the end of this time, the solvent was removed by evaporation under reduced pressure, and the residue was washed with ethanol, to give 2.30 g of a pale yellow powder. The whole of this powder was dissolved in 50 ml of water, insoluble materials were removed by filtration, and the filtrate was adjusted to a pH value of 7.5 by the addition of a 1N aqueous solution of sodium hydroxide. The crystals which precipitated were collected by filtration and washed with water and with ethanol, in that order, to give 1.74 g of the title compound as fine pale yellow needles, melting at 223°–225° C.

Mass Spectrum (CI): m/e 412 (M$^+$+1).

Elemental analysis: Calculated for $C_{19}H_{20}F_3N_3O_4.H_2O$: C, 53.14%; H, 5.17%; N, 9.79%. Found: C, 53.44%; H, 4.93%; N, 9.77%.

EXAMPLE 2

1-Cyclopropyl-8-difluoromethoxy-6-fluoro-7-(3-methylpiperazinyl)-1,4-dihydro-4-oxoquinoline-3-carboxylic acid hydrochloride 240 ml (0.0024 moles) of 1N aqueous hydrochloric acid were added to a suspension of 1.00 g (0.0024 moles) of 1-cyclopropyl-8-difluoromethoxy-6-fluoro-7-(3-methylpiperazinyl)-1,4-dihydro-4-oxoquinoline-3-carboxylic acid (prepared as described in Example 1) in 50 ml of methanol to obtain a transparent solution. This was concentrated by evaporation under reduced pressure, and the residue was washed with ethanol, to give 0.97 g of the title compound (hydrochloride) as a colorless powder, melting at 277°–287° C. (with decomposition).

Elemental analysis: Calculated for $C_{19}H_{21}ClF_3N_3O_4$: C, 50.95%; H, 4.73%; N, 9.38%. Found: C, 50.84%; H, 4.44%; N, 9.29%.

EXAMPLE 3

1-Cyclopropyl-8-difluoromethoxy-6-fluoro-7-(3-methylpiperazinyl)- 1,4-dihydro-4-oxoquinoline-3-carboxylic acid methanesulfonic acid salt 0.093 g (0.00097 moles) of methanesulfonic acid was added to a suspension of 0.40 g of 1-cyclopropyl- 8-difluoromethoxy-6-fluoro-7-(3-methylpiperazinyl)- 1,4-dihydro-4-oxoquinoline-3-carboxylic acid (prepared as described in Example 1) in 50 ml of methanol to obtain a transparent solution. This was concentrated by evaporation under reduced pressure, and the residue was washed with ethanol, to give 0.47 g of the title compound (methanesulfonic acid salt) as a colorless powder, melting at 289°–292° C. (with decomposition).

Elemental analysis: Calculated for $C_{20}H_{24}F_3N_3O_7S.½H_2O$: C, 46.51%; H, 4.88%; N, 8.14%. Found: C, 46.44%; H, 4.65%; N, 7.97%.

EXAMPLES 4 TO 29

Following a procedure similar to that described in Example 1, 2 or 3, the following compounds were produced.

TABLE 3

| Ex No. | Cpd. No. | hydrate, salt etc | m.p. (°C.) |
|---|---|---|---|
| 4 | 34 | hydrate | 220–221 |
| 5 | 34 | hydrochloride, sesquihydrate | 218–224 |
| 6 | 34 | methanesulfonate | 282–284 (decomp.) |
| 7 | 5 | hydrochloride, sesquihydrate | 247–251 |
| 8 | 43 | hydrate cis | 187–188 |
| 9 | 39 | hydrochloride | 249–253 |
| 10 | 3 | hydrate cis | 240–241 |
| 11 | 3 | hydrochloride, hydrate cis (gradual decomposition from 295) | >300 |
| 12 | 3 | methanesulfonate cis | >300 |
| 13 | 32 | hydrochloride, dihydrate | 213–217 |
| 14 | 45 | sesquihydrate | 167–170 |
| 15 | 1 | hydrate | 265–268 (decomp.) |
| 16 | 179 | hydrate | 251–253 |

TABLE 3-continued

| Ex No. | Cpd. No. | hydrate, salt etc | m.p. (°C.) |
|---|---|---|---|
| 17 | 148 | hydrate | (decomp.) 232–237 |
| 18 | 152 | — | 226–229 |
| 19 | 188 | sesquihydrate cis | 241–245 (decomp.) |
| 20 | 149 | — cis | 237–241 |
| 21 | 147 | hydrate | 249–251 |
| 22 | 72 | hydrochloride, sesquihydrate | 230–235 |
| 23 | 59 | hydrochloride, hemihydrate | 252–255 |
| 24 | 73 | hydrochloride | 228–235 (decomp.) |
| 25 | 46 | hydrate | 269–271 (decomp.) |
| 26 | 48 | hydrate | 160–163 |
| 27 | 2 | hydrochloride (3-carbon atom of piperazinyl is in the R configuration | 283–289 (decomp.) |
| 28 | 2 | hydrochloride (3-carbon atom of piperazinyl is in the S configuration | 283–286 (decomp.) |
| 29 | 56 | hydrochloride, sesquihydrate | 270–275 (decomp.) |

EXAMPLE 30

5-Amino-1-cyclopropyl-8-difluoromethoxy-6-fluoro-7-(3-methylpiperazinyl)-1,4-dihydro-4-oxoquinoline-3carboxylic acid 1.30 g (0.013 moles) of 2-methylpiperazine was added to a solution of 0.90 g (0.0026 moles) of 5-amino-1-cyclopropyl- 8-difluoromethoxy-6,7-difluoro-1,4-dihydro- 4-oxoquinoline-3-carboxylic acid (prepared as described in Preparation 11) in 8 ml of pyridine, and the mixture was stirred at 105°–110° C. for 2 hours. At the end of this time, the solvent was removed by distillation under reduced pressure. Water was added to the residue, and the resulting mixture was neutralized (to about pH 7) by the addition of acetic acid; the mixture was then extracted with chloroform. The extract was washed with water, dried over anhydrous sodium sulfate, and concentrated by evaporation under reduced pressure. The resulting residue was washed with ethanol to give 0.72 g of 5-amino-1-cyclopropyl-S-difluoromethoxy-6-fluoro-7-(3-methylpiperazinyl)-1,4-dihydro-4-oxoquinoline-3-carboxylic acid as a yellow powder, melting at 283°–286° C.

Elemental analysis: Calculated for $C_{19}H_{21}F_3N_4O_4$: C, 53.52%; H, 4.96%; N, 13.14%. Found: C, 53.35%; H, 4.93%; N, 13.00%.

EXAMPLES 31 TO 60

Following a procedure similar to that described in Example 30, the following compounds were obtained.

TABLE 4

| Ex No. | Cpd. No. | hydrate, salt etc | m.p. (°C.) |
|---|---|---|---|
| 31 | 107 | hemihydrate | 242–245 |
| 32 | 74 | hemihydrate | 282–283 |
| 33 | 78 | hemihydrate | >300 |
| 34 | 76 | dihydrate cis | 297–300 |
| 35 | 116 | — cis | 244–245 |
| 36 | 76 | hydrochloride cis | >300 |

TABLE 4-continued

| Ex No. | Cpd. No. | hydrate, salt etc | m.p. (°C.) |
|---|---|---|---|
| 37 | 75 | hydrochloride, hemihydrate | 296–298 (decomp.) |
| 38 | 75 | hemihydrate (3-carbon atom of piperazinyl is in the R configuration | 278–281 |
| 39 | 75 | sesquihydrate (3-carbon atom of piperazinyl is in the S configuration | 278–281 |
| 40 | 129 | — | 275–280 (decomp.) |
| 41 | 93 | hydrate | 264–266 (decomp.) |
| 42 | 94 | — | 274–275 (decomp.) |
| 43 | 139 | — | 270–273 (decomp.) |
| 44 | 129 | dihydrate (3-carbon atom of piperazinyl is in the S configuration | 270–275 (decomp.) |
| 45 | 109 | hydrochloride, hemihydrate | 257–259 |
| 46 | 82 | — | 273–274 (decomp.) |
| 47 | 130 | — | 285–291 (decomp.) |
| 48 | 134 | hydrochloride | 255–259 (decomp.) |
| 49 | 144 | hemihydrate (3-carbon atom of diazepinyl is in the S configuration | 252–256 |
| 50 | 131 | — (3-carbon atom of piperazinyl is in the S configuration | 264–267 |
| 51 | 90 | — | 254–257 (decomp.) |
| 52 | 143 | — | 217–221 (decomp.) |
| 53 | 107 | — (3-carbon atom of piperazinyl is in the S configuration | 234–238 |
| 54 | 79 | — | 291–294 (decomp.) |
| 55 | 141 | — | 239–242 (decomp.) |
| 56 | 113 | — | 242–246 (decomp.) |
| 57 | 137 | — | 271–273 (decomp.) |
| 58 | 136 | — | 253–257 (decomp.) |
| 59 | 142 | — | 263–265 (decomp.) |
| 60 | 284 | — | 252–253 (decomp.) |

EXAMPLE 61

Magnesium [5-amino-1-cyclopropyl-8-difluoromethoxy-6-fluoro-7-(3-methylpiperazinyl)-1,4-dihydro-4-oxoquinoline-3-carboxylate]

23.0 ml (0.0023 mole) of a 0.1N aqueous solution of sodium hydroxide were added to 1.00 g (0.00234 mole) of 5-amino-1-cyclopropyl-8-difluoromethoxy-6-fluoro-7-(3-methylpiperazinyl)-1,4-dihydro-4-oxoquinoline-3-carboxylic acid (prepared as described in Example 30), and the resulting insoluble material was removed by filtration. 0.11 g (0.00115 mole) of anhydrous magnesium chloride was added to the filtrate, and the mixture was stirred at room temperature for 90 minutes. At the end of this time, the resulting precipitate was collected by filtration and washed with water, to give 0.91 g of magnesium [5-amino-1-cyclopropyl- 8-difluoromethoxy-6-fluoro-7-(3-methylpiperazinyl)-1,4-dihydro-4-oxoquinoline- 3-carboxylate] as a yellow powder, melting at 291°–293° C. (with decomposition).

Elemental analysis: Calculated for $C_{38}H_{40}F_6N_8O_8Mg \cdot 2H_2O$: C, 50.09%; H, 4.86%; N, 12.29%. Found: C, 50.13%; H, 4.75%; N, 12.19%.

BIOLOGICAL ACTIVITY

The antibacterial activities of a number of compounds of the invention were investigated against a wide variety of bacteria, both Gram-positive and Gram-negative, and the results are shown in the following Tables 5 and 6 in terms of their minimal inhibitory concentrations (μg/ml).

By way of comparison results are also given for the known compound. Norfloxacin, which, for brevity, is identified in the Table as "Compound A". Each compound of the invention is identified by the number of one of the foregoing Examples which illustrates its prepare ion.

TABLE 5

| Micro-organism | | Compound of Ex. No. | | | | | |
|---|---|---|---|---|---|---|---|
| | | 1 | 5 | 30 | 31 | 39 | A |
| Staphylococcus aureus | 209P | 0.05 | <0.01 | <0.01 | <0.01 | <0.01 | 0.2 |
| | 56 | 0.05 | <0.01 | <0.01 | <0.01 | <0.01 | 0.4 |
| | 535 | 0.2 | <0.01 | 0.02 | 0.02 | <0.01 | 6.2 |
| Enterococcus faecalis | 681 | 0.2 | 0.05 | 0.05 | 0.05 | 0.05 | 3.1 |
| Escherichia coli | NIHJ | <0.01 | <0.01 | 0.02 | <0.01 | <0.01 | 0.2 |
| | 609 | 0.4 | 0.4 | 0.2 | 0.2 | 0.05 | 3.1 |
| Salmonella enteritidis | | <0.01 | ≦0.01 | ≦0.01 | ≦0.01 | ≦0.01 | 0.1 |
| Klebsiella pneumoniae | 806 | 0.05 | ≦0.01 | 0.05 | 0.02 | 0.02 | 0.4 |
| | 846 | 0.02 | ≦0.01 | 0.02 | ≦0.01 | ≦0.01 | 0.4 |
| Micro-organism | | Compound of Ex. No. | | | | | |
| | | 1 | 5 | 30 | 31 | 39 | A |
| Enterobacter cloacae | 963 | 0.1 | 0.02 | 0.1 | 0.05 | 0.05 | 0.4 |
| Serratia marcescens | 1184 | 0.4 | 0.1 | 0.4 | 0.2 | 0.2 | 0.2 |
| Proteus vulgaris | 1420 | ≦0.01 | ≦0.01 | ≦0.01 | ≦0.01 | ≦0.01 | 0.02 |
| Morganella morganii | 1510 | 0.1 | 0.02 | 0.2 | 0.1 | 0.2 | 0.05 |
| Pseudomonas aeruginosa | 1001 | 0.4 | 0.4 | 0.4 | 0.4 | 0.2 | 0.8 |

We claim:
1. A compound of the formula

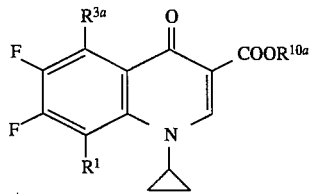

wherein $R^1$ is a fluorinated methoxy group, $R^{10a}$ is a hydrogen atom or a $C_1$–$C_6$ alkyl group and $R^{3a}$ is a hydrogen atom, a nitro group or an amino group.

2. The compound of claim 1, wherein $R^{10a}$ is a $C_1$–$C_6$ alkyl group.

3. The compound of claim 2, wherein $R^1$ is a difluoromethoxy group.

4. The compound of claim 3, wherein $R^{3a}$ is a hydrogen atom.

5. The compound of claim 3, wherein $R^{3a}$ is a nitro group.

6. The compound of claim 3, wherein $R^{3a}$ is an amino group.

7. The compound of claim 1, wherein $R^{10a}$ is a hydrogen atom.

8. The compound of claim 7, wherein $R^1$ is a difluoromethoxy group.

9. The compound of claim 8, wherein $R^{3a}$ is a hydrogen atom.

10. The compound of claim 8, wherein $R^{3a}$ is a nitro group.

11. The compound of claim 8, wherein $R^{3a}$ is an amino group.

12. A compound of the formula

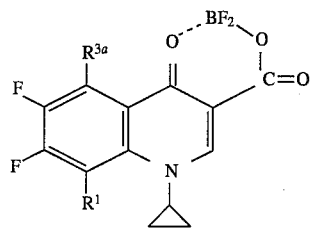

wherein $R^1$ is a fluorinated methoxy group and $R^{3a}$ is a hydrogen atom or an amino group.

13. The compound of claim 12, wherein $R^1$ is a difluoromethoxy group.

14. The compound of claim 13, wherein $R^{3a}$ is a hydrogen atom.

15. The compound of claim 13, wherein $R^{3a}$ is an amino group.

* * * * *

UNITED STATES PATENT AND TRADEMARK OFFICE
CERTIFICATE OF CORRECTION

PATENT NO. : 5,496,951
DATED : March 5, 1996
INVENTOR(S) : IWATA et al

PAGE 1 of 2

It is certified that error appears in the above-identified patent and that said Letters Patent is hereby corrected as shown below:

Title Page, Right Column, under FOREIGN PATENT DOCUMENTS:
    after "0265230" replace "2/1988" with --4/1988--.
    after "0302525" replace "1/1989" with --2/1989--.

Column 1, line 27: replace "Used" with --used--.

Column 8, following line 67 insert:

```
--Ac       acetyl
  Azp      perhydroazepinyl
  Azt      azetidinyl
  Bz       benzyl
  Diz      perhydro-1,4-diazepinyl
              (= homopiperazinyl)
  Et       ethyl
  Etc      ethoxycarbonyl
  Imid     imidazolyl
  Me       methyl
  Mor      morpholino
  Pip      piperidyl
  Piz      piperazinyl
  iPr      isopropyl
  Pyrd     pyrrolidinyl
  Sfo      sulfo
  Thz      perhydro-1,4-thiazin-4-yl
              (= thiomorpholino)--.
```

UNITED STATES PATENT AND TRADEMARK OFFICE
CERTIFICATE OF CORRECTION

PATENT NO. : 5,496,951
DATED : March 5, 1996
INVENTOR(S) : IWATA et al

It is certified that error appears in the above-identified patent and that said Letters Patent is hereby corrected as shown below:

Column 12, lines 53-66: Delete all of the subject matter on these lines.

Column 13, lines 1-6: Delete all of the subject matter on these lines.

Column 34, line 15: replace "Sodium" with --sodium--.

Signed and Sealed this

Twenty-fifth Day of November, 1997

Attest:

BRUCE LEHMAN

Attesting Officer

Commissioner of Patents and Trademarks